(12) United States Patent
Koh et al.

(10) Patent No.: US 7,094,908 B2
(45) Date of Patent: Aug. 22, 2006

(54) **REDUCTION OF CARBONYL COMPOUNDS USING THE CARBONYL REDUCTASE OF *KLUYVEROMYCES MARXIANUS***

(75) Inventors: Hun Yeong Koh, Gyeonggi-Do (KR); Kyung Il Choi, Seoul (KR); Yong Seo Cho, Seoul (KR); Ae Nim Pae, Seoul (KR); Joo Hwan Cha, Seoul (KR); Ye Sun Han, Seoul (KR); Jong Soo Lee, Gyeonggi-Do (KR); Hong Chul Yun, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 324 days.

(21) Appl. No.: 10/327,793

(22) Filed: Dec. 23, 2002

(65) Prior Publication Data

US 2003/0139464 A1    Jul. 24, 2003

(30) Foreign Application Priority Data

Dec. 28, 2001    (KR)    ............................... 2001-87362

(51) Int. Cl.
 *C20D 209/48*    (2006.01)
(52) U.S. Cl. ...................... 548/479; 548/485
(58) Field of Classification Search ............... 548/485
   See application file for complete search history.

(56) References Cited

U.S. PATENT DOCUMENTS 4,927,507 A    5/1990    Schneider et al.

OTHER PUBLICATIONS

Lubouch et al., Aminocarboxyclic Acids. IX. Conformational Studies of RR,SS,and RS,SR-Beta- Hydroxyaspartic Acid Derivatives. Roczniki chemli (1974), 48(12), 2181-9.*
Walter Durckheimer, et al., "Recent Developments in the Field of B-Lactam Antibiotics", Angew. Chem. Int. End. Engl. 24 (1985) 180-202.
Paul J. Reider, et al., "Total Synthesis of Thienamycin: A New Approach From Aspartic Acid", Tetrahedron Letters, vol. 23, No. 22, pp. 2293-2296, 1982.
R. Noyori, et al., "Stereoselective Hydrogenation via dynamic Kinetic Resolution", J. Am. Chem. Soc. 1989, 111, pp. 9134-9135.
Isao Sada, et al., "Process for preparing 4-acetoxy-3-hydroxyethylazatidin-2-one derivatives as antibiotic intermediates", Chem. Abstr., 1989, 110(17), 154035a.

Masayoshi Murata, et al., "Process for preparing optically active 3-substituted azetidinones", Chem. Abstr., 1991, 115(11), 112844c.
S. Servi, "Baker's Yeast as a Reagent in Organic Synthesis", Synthesis, 1990, pp. 1-25.
R. Cauk, et al., "Baker's Yeast Mediated Transformations in Organic Chemistry", Chem. Rev. 1991, vol. 91, pp. 49-97.

* cited by examiner

*Primary Examiner*—Kamal A. Saeed

(57) ABSTRACT

A compound represented by a general formula (Ia) or (Ib) and a stereo-selective preparation method thereof using a carbonyl reductase which is separated from *Kluyveromyces marxianus*. The compound can be prepared by reduction of substituted β-keto ester and can be used as an intermediate in preparing β-lactam group antibiotics.

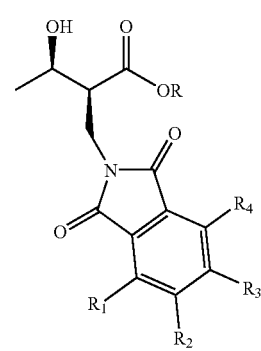

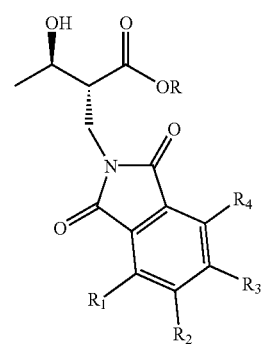

13 Claims, No Drawings

REDUCTION OF CARBONYL COMPOUNDS USING THE CARBONYL REDUCTASE OF KLUYVEROMYCES MARXIANUS

BACKGROUND OF THE INVENTION

1. Field of the Invention

The present invention relates to a compound which is represented by the following formula (Ia) or (Ib), and which can be used as an important intermediate for preparing β-lactam group antibiotics, and to a stereo-selective preparation method thereof.

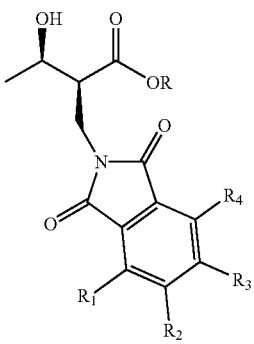

Ia

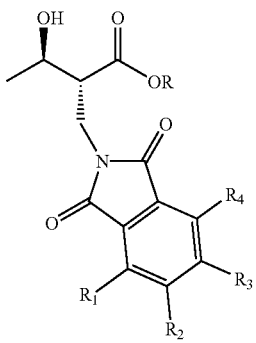

Ib

2. Description of the Background Art

Compound A, B and C represented by the following formulae are important intermediates which can be used in preparing β-lactam group antibiotics.

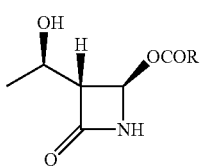

A

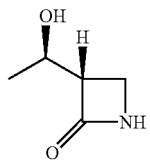

B

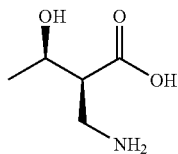

C

As the importance of β-lactam group antibiotics (*Angew. Chem., Int. Ed. Engl.,* 1985, 24, 180) has been increased, the compound C has been used as an important intermediate for preparing (1'R,3R)-4-acyloxy-3-(1'-hydroxy-ethyl)azetidin-2-one (compound A) which requires a stereochemical characteristics. Therefore, synthetic methods of the intermediate compound C have been spotlighted. Currently, preparation of compound A has been attempted with various chiral preparation units, namely, L-aspartamic acid (P. J. Reider, *Tetrahedron Lett.,* 1982, 23, 2293), 2-benzamidomethyl-3-hydroxybutyrate (R. Noyori, *J. Am. Chem. Soc.,* 1989, 111, 9134), (3R)-hydroxybutyrate (I. Sada, *Eur. Pat. Appl.* 280962 (*Chem. Abstr.,* 1989, 110 (17), 154035s)) and the like. A preparation method through a classical resolution of racemic intermediates has been also attempted (M. Masayoshi, *Eur. Pat. Appl.* 421283 (*Chem. Abstr,* 1991, 115 (11), 1128442e)).

(1'R,3S)-3-(1'-t-butyldimethylsilyloxy)azetidin-2-one which is a derivative of the compound B has been known as a useful starting material for preparing β-lactam group antibiotics. It is because that all of commonly used penicillin antibiotics, cephalosporin antibiotics, carbapenem antibiotics which are expected to be antibiotics of the next generation and the like have an azetidin-2-one skeleton.

As a preparation method of (1'R,3S)-3-(1'-t-butyldimethylsilyloxy)azetidin-2-one, there has been reported a method of Noyori et al. (*J. Am. Chem. Soc.* 111, 9134, 1989; and Japan Patent No. 2134349), and a method of a pharmaceutical company in Swiss (U.S. Pat. No. 4,927,507).

The method of Noyori et al. is performed by introducing asymmetric hydrogen to 2-amidomethyl acetoacetate ester, hydrolyzing with an acid to lactamize, and then performing silylation. The method of Noyori et al. uses a stereoselective hydrogenation reaction. However, since an amide is used as a starting material, a strong acid must be used in hydrolysis, and since protection of hydroxy group is performed after the lactamization, it is difficult to perform the lactamization. Besides, separation and purification processes are complicated.

The method of a pharmaceutical company in Swiss comprises sequential steps of a reduction of 2-amidomethyl acetoacetate ester with yeast to obtain a 2-amidomethyl-3-hydroxy butanoic acid ester, a substitution of 2-amidomethyl-3-hydroxy butanoic acid ester into a 5,6-dihydro-(1H,3H,4H)-oxazinyl-5-carboxylic acid ester derivative, an isomerization so as to have a desirable stereochemistry, hydrolysis, lactamization and silylation. However, this method does not seem to be practical in that the obtained product may be hydrolyzed because diasteromers are separated after introducing 2-amidomethyl-3-hydroxy butanoic acid ester into 5,6-dihydro-(1H,3H,4H)-oxazinyl-5-carbonic acid ester derivative, procedures of separation and purification of diastereomers are also complicated, and it has too many steps.

The compound B can be also prepared from a α-substituted β-hydroxy ester, such as the compound C, and the compound C can be prepared from a α-substituted β-keto ester.

As described above, since the compounds A and B can be used as important intermediates for preparing of β-lactam group antibiotics and can be prepared from the compound C, it is necessary to provide a preparation method of the compound C.

Recently, there have been continuous attempts to selectively synthesize an optical isomer which exhibits a useful biological activity among racemic compounds. To achieve this purpose, there have been developed a method using biological catalyst which is different from the conventional organic-chemical preparation method. The preparation method using the biological catalyst is advantageous in that it is more convenient than the conventional organic-chemical preparation method, and it is not necessary to use a poisonous chemical reagent.

Biological catalysis is spotlighted because of its stereoselectivity including an optical isomeric or diastereomeric selectivity. Therefore, a reaction using an enzyme is a very useful experimental method for preparing optically pure compounds. Particularly, a reaction using Baker's Yeast (BY) has been generally used in reduction of carbonyl compounds. However, according to a recently disclosed preparation method, it has been reported that the reduction of a carbonyl group of β-keto ester using Baker's Yeast (BY) generally generates (S)-3-hydroxy compound (S. Servi, *Synthesis*, 1990, 1; R. Csuk, *Chem. Rev.*, 1991, 91, 49). That is, there have not been reported any preparation methods of a (R)-3-hydroxy compound by reducing the carbonyl group of β-keto ester.

SUMMARY OF THE INVENTION

Therefore, an object of the present invention is to provide an α-substituted β-hydroxy ester derivative which can be used as an important intermediate for preparing β-lactam group antibiotics and have a (2S,3R)-stereochemistry, and to provide a stereo-selective preparation method thereof.

DETAILED DESCRIPTION OF THE INVENTION

Reference will now be made in detail to the preferred embodiments of the present invention, examples of which are illustrated in the accompanying drawings.

Generally, while Baker's Yeast (BY) produces a (S)-3-hydroxy compound by reducing a carbonyl group of β-keto ester, a reductase which is separated from *Kluyveromyces marxianus*, used as a reducing catalyst in the present invention, produces (R)-3-hydroxy compounds. *Kluyveromyces marxianus* is one of microorganisms which has not been known well. Particularly, in the present invention, enzymatic reactions are respectively performed using two kinds of reductases which are separated from the Baker's Yeast and *Kluyveromyces marxianus*. Each diastereomer produced with those two reductases is identified by comparing with a chemically synthesized comparative substance, using HPLC and NMR instruments.

In the present invention, an α-substituted β-hydroxy ester derivative having a (2S,3R) stereochemistry, that is, the compound represented by the following chemical formula (Ia) or (Ib) is provided through an enzymatic reaction:

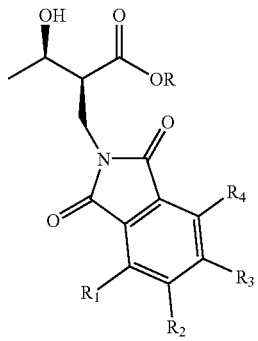

Ia

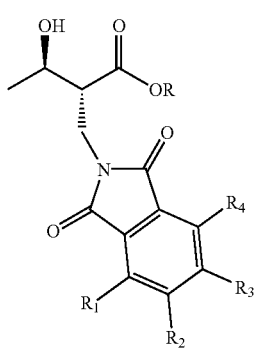

Ib wherein, R represents a saturated or unsaturated alkyl such as methyl, ethyl, propyl, isopropyl, isobutyl and allyl, or aryl such as phenyl; and $R_1$, $R_2$, $R_3$ and $R_4$ are substituents which are present in the benzene ring, and are independently selected from the group consisting of a hydrogen atom, a halogen atom such as Br, Cl, F or I, an alkyl group having 1–4 carbon atoms such as methyl, ethyl and the like, hydroxy, an alkoxy group having 1–4 carbon atoms such as methoxy, an ester group such as acetoxy, phenyl and combinations thereof.

The compound of the present invention represented by formula (Ia) or (Ib) can be used as an intermediate in synthesizing β-lactam group antibiotics.

In the present invention, the compound represented by the following general formula (VI) is used as a substrate in reduction with a reductase:

wherein, R, $R_1$, $R_2$, $R_3$ and $R_4$ are the same as defined in the compound of formula (Ia) or (Ib).

The compound represented by the formula (VI) can be prepared through five steps as shown in the following reaction schemes 1 to 3.

Reaction Scheme 1

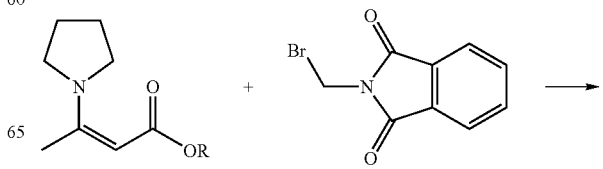

-continued

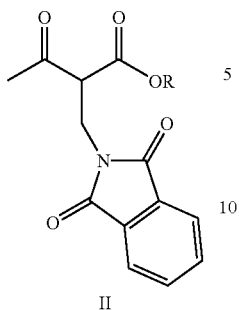

II

In the first step, an enamine of β-keto ester is reacted with N-bromomethyl phthalimide to obtain a compound represented by the formula (II). Examples of available solvent include dimethylformamide, dimethylsulfoxide and the like. It is desirable that the reaction is carried out at room temperature for 5–20 hours.

Reaction Scheme 2

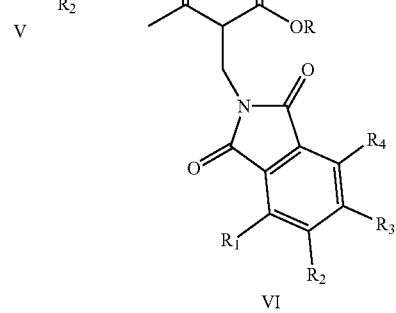

A ketone group of the compound of formula (II) is protected with an appropriate protecting group to obtain a compound of formula (III). An example of protecting reaction for the ketone group is a dehydration with ethylene glycol. The compound of formula (III) is then reacted with hydrazine at about 50° C. to remove phthalimide, and thereby to obtain a primary amine compound of the formula (IV).

Reaction Scheme 3

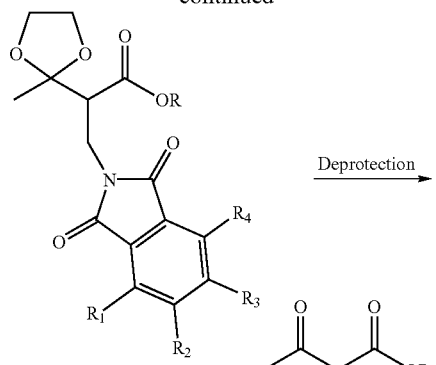

V

VI

The compound having a formula (IV) is reacted in chloroform with a phthalic anhydride derivative having substituents in benzene ring, to obtain the compound having a formula (V). The protecting group of the compound of the formula (V) is removed to obtain a compound having a formula (VI), which is used in an enzymatic reduction as a substrate.

A reduction reaction with an enzyme of the present invention is carried out according to the following reaction scheme 4.

Reaction Scheme 4

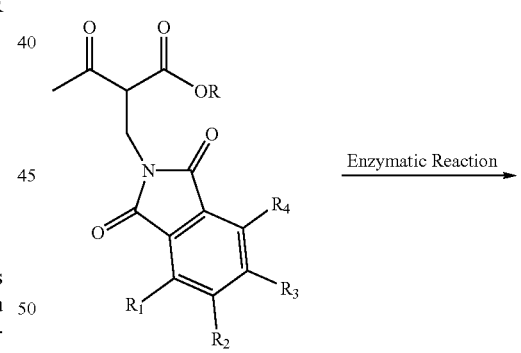

VI

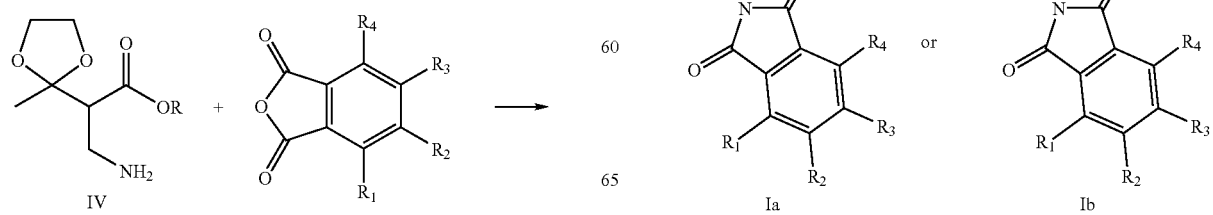

Ia    or    Ib

The compound having the general formula (VI) is mixed with β-NADPH and a buffer solution, the reductase which was separated from *Kluyveromyces marxianus* is then added to the obtained mixture, and the reduction reaction is carried out. It is preferable that pH of the buffer solution is adjusted in the range of 5.0–8.0, and, most preferably, adjusted to 6.8. It is preferable that the reaction temperature is in the range of 20–40° C., and 30° C. is the most preferable. It is possible that the reaction is performed for 5 hours to 5 days, and most preferably performed for 24 hours. Product obtained through the above enzymatic reduction is identified by comparing it with the identical compound prepared by a known chemical method.

In the above reaction schemes 1–4, the substituents R, $R_1$, $R_2$, $R_3$ and $R_4$ are the same as defined in the compound having the formula (Ia) or (Ib).

To demonstrate the usefulness of the enzymatic reduction of the present invention, reduction reactions of the following representative substrate compounds (VIa)–(VIe) with the reductase of *Kluyveromyces marxianus* were carried out, and the results are shown in below Table (1).

TABLE 1

| Compound | Reaction time (hrs) | Conversion Ratio (%) | Ratio of Diastereomers (2S, 3R):(2R, 3R) |
|---|---|---|---|
| VIa | 24 | 99 | 1.0:9.0 |
| VIb | 24 | 91 | 12.0:1.0 |
| VIc | 24 | 93 | 20.0:1.0 |
| VId | 24 | 80 | 11.0:1.0 |
| VIe | 24 | 81 | 8.0:1.0 |

EXAMPLES

Hereinafter, the present invention will now be described in more detail with reference to the following examples. However, the examples are only to illustrate the present invention and do not limit the spirit and scope of the present invention by any of the details of the description.

1. Syntheses of Substrate Compounds

Example 1

Preparation of Starting Materials for Synthesizing Substrate Compounds (1) Methyl 3-tetrahydropyrrolyl-2-butenoate Methyl acetoacetate (20 g, 172.23 mmol) was dissolved in 250 mL of toluene, and then pyrrolidine (43 ml, 516.70 mmol) and p-toluenesulfonic acid hydrate (about 100 mg) were added dropwise. After installing a Dean-Stark separator to the reactor, the reaction mixture was refluxed 140° C. for two days, and then solvent was removed by concentrating the resulting mixture under a reduced pressure, thereby to obtain the desired product (29 g, 99%).

$^1$H NMR (CDCl$_3$, 300 MHz) δ 4.41 (s, 1H, —C═CH—), 3.57 (s, 3H, —COCH$_3$), 3.32–3.17 (brs, 4H, pyrrolidine), 2.42 (s, 3H, CH$_3$), 1.89 (s, 4H, pyrrolidine)

$^{13}$C NMR (CDCl$_3$, 300 MHz) δ 169.9, 160.1, 129.3, 128.6, 125.6, 83.0, 50.2, 48.3, 25.5, 17.0

(2) Ethyl 3-tetrahydropyrrolyl-2-butenoate

Ethyl 3-tetrahydropyrrolyl-2-butenoate was prepared (21 g, 99%) from ethyl acetoacetate (15.0 g, 115.26 mmol) and pyrrolidine (71.1 mL, 345.78 mmol) in the same manner as described in the above Example 1 (1), and the obtained product was identified with the following NMR data.

$^1$H NMR (CDCl$_3$, 300 MHz) δ 4.37 (s, 1H, —C═CH—), 4.00(q, 2H, —OCH$_2$CH$_3$, J=7.1 Hz), 3.22 (brs, 4H, pyrrolidine), 2.38 (s, 3H, —CH$_3$), 1.85 (s, 4H, pyrrolidine), 1.17 (t, 3H, —OCH$_2$CH$_3$, J=7.1 Hz)

$^{13}$C NMR (CDCl$_3$, 300 MHz) δ 169.5, 159.9, 83.6, 58.4, 48.2, 25.5, 17.0, 15.1

(3) Allyl 3-tetrahydropyrrolyl-2-butenoate

Allyl 3-tetrahydropyrrolyl-2-butenoate was prepared (4.7 g, 68%) in the same manner as described in the above Example 1 (1) from allyl acetoacetate (5.0 g, 35.17 mmol) and pyrrolidine (8.8 mL, 105.51 mmol), and the obtained product was identified with the following $^1$H NMR data.

$^1$H NMR (CDCl$_3$, 300 MHz) δ 5.91 (m, 1H, —OCH$_2$CH═CH$_2$), 5.28 (m, 1H, —OCH$_2$CH═CH$_2$), 5.12 (m, 1H, —OCH$_2$CH═CH$_2$), 4.48 (d, 2H, —OCH$_2$CH═CH$_2$), 4.43 (s, 1H, C═CHCO$_2$—), 3.22 (brs, 4H, pyrrolidine), 2.42 (s, 3H, CH$_3$), 1.96 (m, 4H, pyrrolidine)

Example 2

Preparation of Compound (II)

(1) Methyl 2-(phthalimido)methyl-3-oxobutanoate

Methyl 3-tetrahydropyrrolyl-2-butenoate (29.0 g, 171.3 mmol) and N-(bromomethyl)phthalimide (43 g, 179.91 mmol) were dissolved in 250 ml of dimethylformamide, and the resulting mixture was then stirred at room temperature for 16 hours under a nitrogen atmosphere. After checking completion of the reaction with TLC, 1N HCl and water were added into the reaction mixture. The produced solid was filtered under a reduced pressure while washing with hexane and then recrystallized in 100% ethanol, thereby to obtain the desired product (32.26 g, 68%).

$^1$H NMR (CDCl$_3$, 300 MHz) δ 7.70 (m, 2H, ph), 7.60 (m, 3H, ph), 4.04 (m, 2H, —CHCH$_2$NPht), 3.91 (dd, 1H, —CHCH$_2$NPht, J=8.1 Hz, J'=6.6 Hz), 3.61 (s, 3H, —CO$_2$CH$_3$), 2.16 (s, 3H —COCH$_3$)

$^{13}$C NMR (CDCl$_3$, 300 MHz) δ 200.8, 168.5, 168.2, 134.5, 132.1, 123.8, 57.6, 53.3, 36.3, 29.3

(2) Ethyl 2-(phthalimido)methyl-3-oxobutanoate

Ethyl 2-(phthalimido)methyl-3-oxobutanoate was prepared (14.2 g, 52%) in the same manner as described in the above Example 2 (1) from ethyl 3-tetrahydropyrrolyl-2-butenoate (17.3 g, 94.68 mmol) and N-(bromomethyl)phthalimide (25.0 g, 104.14 mmol). The obtained product was identified with the following NMR data.

$^1$H NMR (CDCl$_3$, 300 MHz) δ 7.77 (m, 2H, ph), 7.65 (m, 2H, ph), 4.14 (m, 4H, —OCH$_2$CH$_3$, —CHCH$_2$NPht), 3.96 (t, 1H, —CHCH$_2$NPht, J=6.6 Hz), 2.22 (s, 3H —COCH$_3$), 1.16 (t, 3H, —OCH$_2$CH$_3$, J=6.7 Hz)

$^{13}$C NMR (CDCl$_3$, 300 MHz) δ 200.9, 168.2, 168.0, 134.5, 132.2, 123.8, 62.4, 57.7, 36.3, 29.2, 14.3

(3) Allyl 2-(phthalimido)methyl-3-oxobutanoate

Allyl 2-(phthalimido)methyl-3-oxobutanoate was prepared (6.1 g, 86%) in the same manner as described in the above Example 2 (1) from allyl 3-tetrahydropyrrolyl-2-butenoate (4.6 g, 23.58 mmol) and N-(bromomethyl)phthalimide (6.22 g, 25.94 mmol), and the obtained product was identified with the following NMR data.

1H NMR (CDCl$_3$, 300 MHz) δ 7.83 (m, 2H, phenyl), 7.72 (m, 2H, phenyl), 5.85 (m, 1H, —OCH$_2$CH═CH$_2$), 5.21 (m, 2H, —OCH$_2$CH═CH$_2$), 5.21 (m, 1H, —OCH$_2$CH═CH$_2$), 4.62 (t, 2H, —CHCH$_2$NPht), 4.51 (s, 2H, —OCH$_2$CH═CH$_2$), 4.20 (m, 1H, —CHCH$_2$NPht), 2.30 (d, 3H, CH$_3$, J=6.0 Hz).

Example 3

Preparation of Compound (III)

(1) Methyl 2-phthalimidomethyl-3-ethylenedioxobutanoate

After methyl 3-tetrahydropyrrolyl-2-butenoate (24.0 g, 87.19 mmol) and ethylene glycol (9.7 ml, 174.38 mmol) were dissolved in 300 ml of toluene, a catalytic amount of p-toluenesulfonic acid hydrate (about 300 mg) was added to the obtained solution. After installing Dean-Stark separator, the resulting mixture was refluxed at 140° C. for 16 hours. After checking out completion of reaction with TLC, saturated aqueous $NaHCO_3$ solution was added to the reaction mixture. The organic layer was washed with water, dried with anhydrous sulfate salt, and then concentrated under a reduced pressure. The residue was purified by performing column chromatography (eluent: n-hexane/ethyl acetate=3/1), thereby to obtain the desired product (26 g, 93%).

$^1$H NMR ($CDCl_3$, 300 MHz) δ 7.76 (dd, 2H, ph, J=5.6 Hz, J'=3.1 Hz), 7.64 (m, 3H, ph), 3.98–3.87 (m, 6H, acetal H, —CHCH$_2$NPht), 3.60 s, 3H, —CO$_2$CH$_3$), 3.22 dd, 1H, —CHCH$_2$NPht, J=8.8 Hz, J'=5.5 Hz), 1.44 (s, 3H, —CH$_3$)

$^3$C NMR $CDCl_3$, 300 MHz) δ 171.3, 168.3, 134.6, 134.4, 132.4, 123.8, 123.7, 108.9, 65.9, 65.1, 52.6, 51.9, 37.0, 22.1.

(2) Ethyl 2-phthalimidomethyl-3-ethylenedioxobutanoate

Ethyl 2-phthalimidomethyl-3-ethylenedioxobutanoate was prepared (16.0 g, 98%) in the same manner as described in the above Example 3 (1) from ethyl 3-tetrahydropyrrolyl-2-butenoate (14.1 g, 48.91 mmol) and ethylene glycol (6.0 mL, 107.60 mmol), and the obtained product was identified with the following NMR data.

$^1$H NMR $CDCl_3$, 300 MHz) δ 7.76 m, 2H, ph), 7.64 m, 2H, ph), 4.02 (m, 4H, —OCH$_2$CH$_3$, —CHCH$_2$NPht), 3.88 m, 4H, acetal H), 3.22 (d, 1H, —CHCH$_2$NPht), 1.44 (s, 3H, —CH$_3$), 1.08 (t, 3H, —OCH$_2$CH$_3$, J=7.1 Hz)

$^{13}$C NMR ($CDCl_3$, 300 MHz) δ 170.8, 168.2, 134.4, 132.3, 123.6, 108.9, 65.3, 65.0, 61.3, 51.9, 36.9, 22.1, 14.3

(3) Allyl 2-phthalimidomethyl-3-ethylenedioxobutanoate

Allyl 2-phthalimidomethyl-3-ethylenedioxobutanoate was prepared (4.8 g, 75%) in the same manner as described in the above Example 3 (1) from allyl 3-tetrahydropyrrolyl-2-butenoate (5.7 g, 18.00 mmol) and ethylene glycol (2.1 mL, 37.00 mmol), and the obtained product was identified with the following NMR data.

$^1$H NMR ($CDCl_3$, 300 MHz) δ 7.73 (t, 2H, phenyl), 7.63 (t, 2H, phenyl), 5.72 (m, 1H, —OCH$_2$CH=CH$_2$), 5.15 (m, 1H, —OCH$_2$CH=CH$_2$, J=12.0 Hz), 5.01 (m, 1H, —OCH$_2$CH=CH$_2$, J=12.0 Hz), 4.47 (d, 2H, —OCH$_2$CH=CH$_2$, J=6 Hz), 3.99 (m, 2H, —CHCH$_2$NPht), 3.88 (m, 4H, acetal H), 3.23 (q, 1H, —CHCH$_2$NPht), 1.42 (s, 3H, CH$_3$)

Example 4

Preparation of Compound (IV)

(1) Methyl 2-aminomethyl-3-ethylenedioxobutanoate

Methyl 2-phthalimidomethyl-3-ethylenedioxobutanoate (26.0 g, 81.44 mmol) was dissolved in 250 ml of ethanol, and hydrazine monohydrate (12.2 g, 244.31 mmol) was then slowly add to the obtained solution. The resulting mixture was then refluxed at 90° C. for 1 hour. After the reaction was completed, a saturated aqueous $NaHCO_3$ solution was added to the reaction mixture. The organic layer was washed with water, and the aqueous layer was extracted with dichloromethane. The combined organic extracts were sufficiently washed with a saturated aqueous $NaHCO_3$ solution so as to be about pH 11, dried with anhydrous sulfate, and then concentrated under a reduced pressure, thereby to obtain an oily product (11.0 g, 72%).

$^1$H NMR ($CDCl_3$, 300 MHz) δ 3.90 (m, 4H, acetal H), 3.67 (s, 3H, —CO$_2$CH$_3$), 2.99 (m, 2H, —CHCH$_2$NH$_2$), 2.73 (m, 1H, —CHCH$_2$NH$_2$), 1.31 (s, 3H, —CH$_3$)

$^3$C NMR ($CDCl_3$, 300 MHz) δ 172.8, 109.2, 65.2, 65.1, 52.0, 41.1, 22.4

(2) Ethyl 2-aminomethyl-3-ethylenedioxobutanoate

Ethyl 2-aminomethyl-3-ethylenedioxobutanoate was prepared (9.3 g, 95%) in the same manner as described in the above Example 4 (1) from ethyl 2-phthalimidomethyl-3-ethylenedioxobutanoate (16.0 g, 47.99 mmol) and hydrazine monohydrate (6.9 g, 143.97 mmol), and the obtained product was identified with the following NMR data.

$^1$H NMR ($CDCl_3$, 300 MHz) δ 4.11 (q, 2H, —OCH$_2$CH$_3$, J=5.4 Hz), 3.88 (m, 4H, acetal H), 3.00 (m, 1H, —CHCH$_2$NPht), 2.88 (m, 1H, —CHCH$_2$NPht), 2.69 (q, 1H, —CHCH$_2$NPht, J=4.7 Hz), 1.31 (s, 3H, —CH$_3$), 1.21 (t, 3H, —OCH$_2$CH$_3$, J=7.1 Hz)

$^{13}$C NMR ($CDCl_3$, 300 MHz) δ 172.2, 109.2, 65.1, 64.9, 60.9, 58.1, 41.1, 22.4, 22.4, 14.6

(3) Allyl 2-aminomethyl-3-ethylenedioxobutanoate

Allyl 2-aminomethyl-3-ethylenedioxobutanoate was prepared (2.5 g, 88%) in the same manner as described in the above Example 4 (1) from allyl 2-phthalimidomethyl-3-ethylenedioxobutanoate (4.57 g, 13.23 mmol) and hydrazine monohydrate (1.9 mL, 39.68 mmol), and the obtained product was identified with the following NMR data.

$^1$H NMR ($CDCl_3$, 300 MHz) δ 5.89 (m, 1H, —OCH$_2$CH=CH$_2$), 5.30 (q, 1H, —OCH$_2$CH=CH$_2$, J=18.0 Hz), 5.17 (q, 1H, —OCH$_2$CH=CH$_2$, J=18.0 Hz), 4.58 (m, 2H, —OCH$_2$CH=CH$_2$), 3.90 (m, 4H, acetal H), 2.90 (m, 2H, —CHCH$_2$NPht), 2.75 (q, 1H, —CHCH$_2$NPht), 1.70 (brs, 1H, —NH$_2$), 1.32 (s, 3H, CH$_3$)

Example 5

Preparation of Compound (V)

(1) Methyl 3-(1,3-dioxo-1,3,4,5,6,7-hexahydro-isoindol-2-yl)-2-(2-methyl-[1,3]dioxolan-2-yl)propionate Methyl 3-amino-2-(2-methyl-[1,3]di-2-yl)propionate (1.0 g, 5.29 mmol) and 3,4,5,6-tetrahydrophthalic anhydride (1.0 g, 6.34 mmol) were dissolved in 20 mL of chloroform, and the resulting mixture was refluxed at 80° C. for 3 days. After the reaction was completed, the solvent was removed by concentrating the reaction mixture under a reduced pressure. The residue was purified by performing column chromatography (eluent: n-hexane/ethyl acetate=2/1), to obtain the desired product (1.4 g, 80%).

$^1$H NMR ($CDCl_3$, 300 MHz) δ 3.88 (m, 4H, acetal H), 3.71 (m, 2H, —CHCH$_2$NPht), 3.56 (s, 3H, —CO$_2$CH$_3$), 3.00 (m, 1H, —CHCH$_2$NPht), 2.16 (s, 4H, cyclohexane), 1.68 (s, 4H, cyclohexane), 1.34 (s, 3H, —CO$_2$CH$_3$)

$^{13}$C NMR ($CDCl_3$, 75 MHz) δ 171.1, 141.8, 141.7, 108.6, 65.0, 64.8, 52.1, 52.0, 36.4, 21.7, 21.5, 20.0

(2) Methyl 3-(4-fluoro-1,3-dioxo-1,3-dihydro-isoindol-2-yl)-2-(2-methyl-[1,3]dioxolan-2-yl)propionate Methyl 3-(4-fluoro-1,3-dioxo-1,3-dihydro-isoindol-2-yl)-2-(2-methyl-[1,3]dioxolan-2-yl)propionate was prepared (0.24 g, 28%) in the same manner as described in the above example 5 (1) from methyl 3-amino-2-(2-methyl-[1,3]dioxolan-2-yl)propionate (0.50 g, 2.64 mmol) and 3-fluorophthalic anhydride (0.57 g, 3.43 mmol), and the obtained product was identified with the following NMR data.

¹H NMR (CDCl₃, 300 MHz) δ 7.72 (m, 2H, ph), 7.38 (t, 1H, ph, J=9.0 Hz), 4.18–3.98 (m, 3H, —CHCH₂NPht, —CHCH₂NPht), 3.72 (s, 3H —CO₂CH₃), 2.28 (s, 3H, —COCH₃)

³C NMR (CDCl₃, 300 MHz) δ 171.2, 163.9, 157.7, 152.3, 125.5, 121.6, 121.3, 120.5, 108.9, 65.4, 62.9, 60.9, 54.7, 51.7, 37.2, 22.0, 14.5

(3) Methyl 3-(4,7-difluoro-1,3-dioxo-1,3-dihydro-isoindol-2-yl)-2-(2-methyl-[1,3]dioxolan-2-yl)propionate Methyl 3-(4,7-difluoro-1,3-dioxo-1,3-dihydro-isoindol-2-yl)-2-(2-methyl-[1,3]dioxolan-2-yl)propionate was prepared (0.27 g, 31%) in the same manner as described in the above example 5. (1) from methyl 3-amino-2-(2-methyl-[1,3]dioxolan-2-yl)propionate (0.47 g, 2.47 mmol) and 3,6-difluorophthalic anhydride (0.50 g, 2.72 mmol), and the obtained product was identified with the following NMR data.

¹H NMR (CDCl₃, 300 MHz) δ 7.31 (t, 2H, ph, J=5.3 Hz), 3.95 (m, 6H, acetal H, —CHCH₂NPht), 3.64 (s, 3H —CO₂CH₃), 3.20 (m, 1H, —CHCH₂NPht), 1.42 (s, 3H, CH₃)

³C NMR (CDCl₃, 300 MHz) δ 171.9, 163.9, 155.8, 152.2, 125.5, 121.1, 120.6, 120.1, 108.9, 65.4, 60.9, 53.8, 51.7, 37.2, 22.0, 14.5

(4) Methyl 3-(4-nitro-1,3-dioxo-1,3-dihydro-isoindol-2-yl)-2-(2-methyl-[1,3]dioxolan-2-yl)propionate Methyl 3-(4-nitro-1,3-dioxo-1,3-dihydro-isoindol-2-yl)-2-(2-methyl-[1,3]dioxolan-2-yl)propionate was prepared (0.27 g, 28%) in the same manner as described in the above example 5 (1) from methyl 3-amino-2-(2-methyl-[1,3]dioxolan-2-yl)propionate (0.50 g, 2.64 mmol) and 3-nitrophthalic anhydride (0.57 g, 3.43 mmol), and the obtained product was identified with the following NMR data.

¹H NMR (CDCl₃, 300 MHz) δ 8.02 (dd, 2H, ph, J=7.9 Hz, J'=1.0 Hz), 7.83 (t, 1H, ph, J=7.8 Hz), 3.99–3.59 (m, overlapping, 6H, acetal H, —CHCH₂NPht), 3.60 (s, 3H, —CO₂CH₃), 3.20 (m, 1H, —CHCH₂NPh), 1.39 (s, 3H, —COCH₃)

¹³C NMR (CDCl₃, 300 MHz) δ 171.1, 165.8, 163.0, 145.5, 135.8, 129.4, 127.5, 124.0, 108.9, 65.4, 65.1, 52.7, 37.6, 22.1

(5) Methyl 3-(5-nitro-1,3-dioxo-1,3-dihydro-isoindol-2-yl)-2-(2-methyl-[1,3]dioxolan-2-yl)propionate Methyl 3-(5-nitro-1,3-dioxo-1,3-dihydro-isoindol-2-yl)-2-(2-methyl-[1,3]dioxolan-2-yl)propionate was prepared (1.60 g, 42%) in the same manner as described in the above example 5 (1) from methyl 3-amino-2-(2-methyl-[1,3]dioxolan-2-yl)propionate (2.00 g, 10.57 mmol) and 4-nitrophthalic anhydride (0.57 g, 3.43 mmol), and the obtained product was identified with the following NMR data.

¹H NMR (CDCl₃, 300 MHz) δ 7.50 (dd, 1H, ph, J=8.6 Hz, J'=7.3 Hz), 7.29 (d, 1H, ph, J'=7.0 Hz), 7.06 (dd, 1H, ph, J=8.2 Hz), 3.92 (m, overlapping, 6H, acetal H, —CHCH₂NPht), 3.62 (s, 3H, —CO₂CH₃), 3.21 (dd, 1H, —CHCH₂NPht J=8.9 Hz, J'=5.3 Hz), 1.43 (s, 3H, —COCH₃)

¹³C NMR (CDCl₃, 300 MHz) δ 171.0, 165.2, 165.9, 152.1, 136.7, 133.7, 129.8, 125.1, 119.2, 108.9, 65.9, 65.1, 57.1, 52.6, 51.7, 37.5, 36.8, 29.4, 22.0

(6) Methyl 3-(4-methyl-1,3-dioxo-1,3-dihydro-isoindol-2-yl)-2-(2-methyl-[1,3]dioxolan-2-yl)propionate Methyl 3-(4-methyl-1,3-dioxo-1,3-dihydro-isoindol-2-yl)-2-(2-methyl-[1,3]dioxolan-2-yl)propionate was prepared (0.39 g, 52%) in the same manner as described in the above example 5 (1) from methyl 3-amino-2-(2-methyl-[1,3]dioxolan-2-yl)propionate (0.54 g, 2.86 mmol) and 3-methylphthalic anhydride (0.56 g, 3.44 mmol), and the obtained product was identified with the following NMR data.

¹H NMR (CDCl₃, 300 MHz) δ 7.54 (d, 1H, ph, J=7.3 Hz), 7.46 (t, 1H, ph, J=7.4 Hz), 7.35 (d, 1H, ph, J=7.1 Hz), 3.91 (m, overlapping, 6H, acetal H, —CHCH₂NPht), 3.58 (s, 3H, —CO₂CH₃), 3.21 (m, 1H, —CHCH₂NPht), 1.41 (s, 3H, —COCH₃)

¹³C NMR (CDCl₃, 300 MHz) δ 171.4, 168.9, 168.1, 138.2, 136.7, 133.8, 132.7, 128.9, 121.2, 108.9, 65.2, 65.0, 52.4, 52.0, 36.8, 22.0, 17.8.

(7) Methyl 3-(5-methyl-1,3-dioxo-1,3-dihydro-isoindol-2-yl)-2-(2-methyl-[1,3]dioxolan-2-yl)propionate Methyl 3-(5-methyl-1,3-dioxo-1,3-dihydro-isoindol-2-yl)-2-(2-methyl-[1,3]dioxolan-2-yl)propionate was prepared (0.12 g, 10%) in the same manner as described in the above example 5 (1) from methyl 3-amino-2-(2-methyl-[1,3]dioxolan-2-yl)propionate (0.50 g, 2.64 mmol) and 4-methylphthalic anhydride (0.56 g, 3.43 mmol), and the obtained product was identified with the following NMR data.

¹H NMR (CDCl₃, 300 MHz) δ 7.64 (dd, 1H, ph, J=5.1 Hz, J'=2.9 Hz), 7.56 (s, 1H, ph), 7.42 (dd, 1H, ph, J=7.6 Hz, J'=0.6 Hz), 3.99–3.61 (m, overlapping, 6H, acetal H, —CHCH₂NPht), 3.60 (s, 3H, —CO₂CH₃), 3.22 (m, 1H, —CHCH₂NPht), 2.42 (s, 3H, —CH₃), 1.44 (s, 3H, —COCH₃)

¹³C NMR (CDCl₃, 300 MHz) δ 171.4, 168.5, 168.4, 145.6, 134.9, 132.8, 129.8, 124.3, 123.6, 109.0, 65.3, 65.1, 52.6, 52.0, 37.0, 22.4, 22.0.

(8) Methyl 3-(5-t-butyl-1,3-dioxo-1,3-dihydro-isoindol-2-yl)-2-(2-methyl-[1,3]dioxolan-2-yl)propionate Methyl 3-(5-t-butyl-1,3-dioxo-1,3-dihydro-isoindol-2-yl)-2-(2-methyl-[1,3]dioxolan-2-yl)propionate was prepared (0.14 g, 14%) in the same manner as described in the above example 5 (1) from methyl 3-amino-2-(2-methyl-[1,3]dioxolan-2-yl)propionate (0.50 g, 2.64 mmol) and 4-t-butylphthalic anhydride (0.70 g, 3.43 mmol), and the obtained product was identified with the following NMR data.

¹H NMR (CDCl₃, 300 MHz) δ 7.86 (s, 1H, ph), 7.73 (m, 2H, ph), 3.99 (m, 6H, —CHCH₂NPht, acetal H), 3.58 (s, 3H, —CO₂CH₃), 3.28(dd, 1H, —CHCH₂NPht, J=8.3 Hz, J'=6.5 Hz), 1.50 (s, 3H, —COCH₃, 1.33 (s, 9H, —C(CH₃)₃)

¹³C NMR (CDCl₃, 300 MHz) δ 173.0, 171.6, 168.3, 168.4, 158.9, 156.6, 155.1, 134.4, 130.9, 129.7, 127.9, 109.0, 65.3, 62.2, 60.3, 52.5, 36.9, 61.5, 22.1, 14.5.

(9) Methyl 3-(4-hydroxy-1,3-dioxo-1,3-dihydro-isoindol-2-yl)-2-(2-methyl-[1,3]dioxolan-2-yl)propionate Methyl 3-(4-hydroxy-1,3-dioxo-1,3-dihydro-isoindol-2-yl)-2-(2-methyl-[1,3]dioxolan-2-yl)propionate was prepared (0.84 g, 45%) in the same manner as described in the above example 5 (1) from methyl 3-amino-2-(2-methyl-[1,3]dioxolan-2-yl)propionate (1.00 g, 5.54 mmol) and 3-hydroxyphthalic anhydride (1.00 g, 6.09 mmol), and the obtained product was identified with the following NMR data.

¹H NMR (CDCl₃, 300 MHz) δ 7.50 (dd, 1H, ph, J=8.6 Hz, J'=7.3 Hz), 7.29 (d, 1H, ph, J=7.1 Hz), 7.06 (dd, 1H, ph, J=8.3 Hz), 3.92 (m, 6H, acetal, —CHCH₂NPht), 3.62 (s, 3H —CO₂CH₃), 3.21 (dd, 1H, —CHCH₂NPht J=8.9 Hz, J'=5.3 Hz), 1.43 (s, 3H, —COCH₃)

¹³C NMR (CDCl₃, 300 MHz) δ 171.4, 170.3, 167.9, 155.1, 136.8, 132.3, 123.1, 116.4, 114.9, 108.9, 65.4, 65.1, 52.7, 52.0, 36.9, 22.1.

(10) Methyl 3-(4,7-dichloro-1,3-dioxo-1,3-dihydro-isoindol-2-yl)-2-(2-methyl-[1,3]dioxolan-2-yl)propionate Methyl 3-(4,7-dichloro-1,3-dioxo-1,3-dihydro-isoindol-2-yl)-2-(2-methyl-[1,3]dioxolan-2-yl)propionate was prepared (0.23 g, 30%) in the same manner as described in the above example 5 (1) from methyl 3-amino-2-(2-methyl-[1,3]dioxolan-2-yl)propionate (0.40 g, 2.30 mmol) and 3,6- dichlorophthalic anhydride (0.50 g, 2.30 mmol), and the obtained product was identified with the following NMR data.

$^1$H NMR (CDCl$_3$, 300 MHz) δ 7.58 (s, 2H, ph), 4.00 (m, overlapping, 6H, acetal H, —CHCH$_2$NPht), 3.72 (s, 3H, —CO$_2$CH$_3$), 3.29 (dd, 1H, —CHCH$_2$NPht J=8.2 Hz, J'=5.8 Hz), 1.52 (s, 3H, —COCH$_3$)

$^{13}$C NMR (CDCl$_3$, 300 MHz) δ 164.8, 137.3, 65.7, 65.4, 52.9, 52.0, 37.7, 22.5, 10.6.

(11) Methyl 3-(5,6-dichloro-1,3-dioxo-1,3-dihydro-isoindol-2-yl)-2-(2-methyl-[1,3]dioxolan-2-yl)propionate Methyl 3-(5,6-dichloro-1,3-dioxo-1,3-dihydro-isoindol-2-yl)-2-(2-methyl-[1,3]dioxolan-2-yl)propionate was prepared (0.42 g, 39%) in the same manner as described in the above example 5 (1) from methyl 3-amino-2-(2-methyl-[1,3]dioxolan-2-yl)propionate (0.50 g, 2.64 mmol) and 4,5-dichlorophthalic anhydride (0.80 g, 3.64 mmol), and the obtained product was identified with the following NMR data.

$^1$H NMR (CDCl$_3$, 300 MHz) δ 7.84 (s, 2H, ph), 3.90 (m, overlapping, 6H, acetal H, —CHCH$_2$NPht), 3.61 (s, 3H, —CO$_2$CH$_3$), 3.19 (dd, 1H, —CHCH$_2$NPht J=8.1 Hz, J'=6.2 Hz), 1.42 (s, 3H, —COCH$_3$).

(12) Methyl 3-(1,3-dioxo-1,3-dihydro-benzo[f]isoindol-2-yl)-2-(2-methyl-[1,3]dioxolan-2-yl)propionate Methyl 3-(1,3-dioxo-1,3-dihydro-benzo[f]isoindol-2-yl)-2-(2-methyl-[1,3]dioxolan-2-yl)propionate was prepared (51 mg, 48%) in the same manner as described in the above example 5 (1) from methyl 3-amino-2-(2-methyl-[1,3]dioxolan-2-yl)propionate (56 mg, 0.29 mmol) and 2,3-naphthalic anhydride (50 mg, 0.25 mmol), and the obtained product was identified with the following NMR data.

$^1$H NMR (CDCl$_3$, 300 MHz) δ 8.26 (s, 2H, ph), 7.98 (m, 2H, ph), 7.64 (m, 2H, ph), 4.08–3.89 (m, 6H, acetal H, —CHCH$_2$NPht), 3.61 (s, 3H, —CO$_2$CH$_3$), 3.29 (dd, 1H, —CHCH$_2$NPht J=8.2 Hz, J=6.6 Hz), 1.47 (s, 3H, —COCH$_3$)

$^{13}$C NMR (CDCl$_3$, 300 MHz) δ 171.4, 168.0, 138.8, 130.7, 129.6, 128.1, 125.1, 109.1, 65.4, 65.1, 52.6, 51.8, 37.3, 22.1.

(13) Methyl 3-(1,3-dioxo-4-phenyl-1,3-dihydro-benzo[f]isoindol-2-yl)-2-(2-methyl-[1,3]dioxolan-2-yl)propionate Methyl 3-(1,3-dioxo-4-phenyl-1,3-dihydro-benzo[f]isoindol-2-yl)-2-(2-methyl-[1,3]dioxolan-2-yl)propionate was prepared (51 mg, 48%) in the same manner as described in the above example 5 (1) from methyl 3-amino-2-(2-methyl-[1,3]dioxolan-2-yl)propionate (50 mg, 0.25 mmol) and 3-phenylnaphthalic anhydride (0.50 g, 0.25 mmol), and the obtained product was identified with the following NMR data.

$^1$H NMR (CDCl$_3$, 300 MHz) δ 8.29 (s, 1H, ph), 7.99 (d, 1H, ph, J=8.1 Hz), 7.71 (d, 1H, ph, J=8.4 Hz), 7.59 (t, 1H, ph), 7.46 (m, 4H, ph), 7.33 (m, 2H, ph), 3.99–3.83 (m, 6H, —CHCH$_2$NPht, acetal), 3.57 (s, 3H, —CO$_2$CH$_3$), 3.23 (m, 1H, —CHCH$_2$NPht), 1.41 (s, 3H, —COCH$_3$)

$^{13}$C NMR (CDCl$_3$, 300 MHz) δ 171.4, 167.8, 140.6, 135.9, 134.9, 130.8, 129.6, 128.6, 127.9, 124.7, 124.0, 109.0, 65.4, 65.1, 61.7, 52.6, 51.8, 37.2, 22.1, 14.0.

(14) Methyl 3-(2,5-dioxo-3-phenyl-2,5-dihydro-pyrrol-1-yl)-2-(2-methyl-[1,3]dioxolan-2-yl)propionate Methyl 3-(2,5-dioxo-3-phenyl-2,5-dihydro-pyrrol-1-yl)-2-(2-methyl-[1,3]dioxolan-2-yl)propionate was prepared (1.0 g, 56%) in the same manner as described in the above example 5 (1) from methyl 3-amino-2-(2-methyl-[1,3]dioxolan-2-yl)propionate (1.00 g, 5.29 mmol) and phenylmaleic anhydride (1.10 g, 6.34 mmol), and the obtained product was identified with the following NMR data.

$^1$H NMR (CDCl$_3$, 300 MHz) δ 7.83 (m, 2H, ph), 7.36 (m, 3H, ph), 6.65 (s, 1H, —CH=C—), 3.95–3.61 (m, overlapping, 6H, acetal H, —CHCH$_2$NPht), 3.61 (s, 3H, —CO$_2$CH$_3$), 3.15 (dd, 1H, —CHCH$_2$NPht), 1.41 (s, 3H, —COCH$_3$)

$^{13}$C NMR (CDCl$_3$, 300 MHz) δ 171.4, 170.6, 170.3, 144.1, 131.6, 129.5, 129.0, 128.9, 127.3, 124.3, 108.9, 65.3, 65.1, 52.6, 52.0, 37.0, 22.0.

(15) Methyl 3-(2,5-dioxo-3,4-diphenyl-2,5-dihydro-pyrrol-1-yl)-2-(2-methyl-[1,3]dioxolan-2-yl)propionate Methyl 3-(2,5-dioxo-3,4-diphenyl-2,5-dihydro-pyrrol-1-yl)-2-(2-methyl-[1,3]dioxolan-2-yl)propionate was prepared (1.40 g, 72%) in the same manner as described in the above example 5 (1) from methyl 3-amino-2-(2-methyl-[1,3]dioxolan-2-yl)propionate (1.00 g, 5.29 mmol) and 1,2-diphenyl-maleic anhydride (1.60 g, 6.34 mmol), and the obtained product was identified with the following NMR data.

$^{13}$C NMR (CDCl$_3$, 300 MHz) δ 171.7, 171.0, 136.9, 130.6, 129.3, 109.3, 65.6, 65.4, 52.9, 52.4, 37.7, 22.4.

(16) Methyl 3-(5-fluoro-1,3-dioxo-1,3-dihydro-isoindol-2-yl)-2-(2-methyl-[1,3]dioxolan-2-yl)propionate Methyl 3-(5-fluoro-1,3-dioxo-1,3-dihydro-isoindol-2-yl)-2-(2-methyl-[1,3]dioxolan-2-yl)propionate was prepared (0.66 g, 47%) in the same manner as described in the above example 5 (1) from methyl 3-amino-2-(2-methyl-[1,3]dioxolan-2-yl)propionate (0.80 g, 5.07 mmol) and 4-fluorophthalic anhydride (0.80 g, 5.07 mmol), and the obtained product was identified with the following NMR data.

$^1$H NMR (CDCl$_3$, 300 MHz) δ 7.76 (dd, 1H, ph, J=8.2 Hz, J'=4.5 Hz), 7.41 (dd, 1H, ph, J=7.1 Hz, J'=2.2 Hz), 7.32 (t, 1H, ph, J=7.4 Hz), 3.88 (m, 6H, acetal, —CHCH$_2$NPht), 3.58 (s, 3H, —CO$_2$CH$_3$), 3.18 (dd, 1H, —CHCH$_2$NPht, J=8.7 Hz, J'=5.6 Hz), 1.40 (s, 3H, —COCH$_3$)

$^{13}$C NMR (CDCl$_3$, 300 MHz) δ 171.1, 168.4, 167.1, 166.8, 135.1, 135.0, 128.1, 128.0, 126.1, 121.5, 121.2, 111.6, 111.2, 108.8, 65.3, 65.8, 52.4, 51.8, 37.1, 21.9.

(17) Methyl 3-(5-chloro-1,3-dioxo-1,3-dihydro-isoindol-2-yl)-2-(2-methyl-[1,3]dioxolan-2-yl)propionate Methyl 3-(5-chloro-1,3-dioxo-1,3-dihydro-isoindol-2-yl)-2-(2-methyl-[1,3]dioxolan-2-yl)propionate was prepared (0.54 g, 73%) in the same manner as described in the above example 5 (1) from methyl 3-amino-2-(2-methyl-[1,3]dioxolan-2-yl)propionate (0.40 g, 2.11 mmol) and 4-chlorophthalic anhydride (0.50 g, 2.74 mmol), and the obtained product was identified with the following NMR data.

$^1$H NMR (CDCl$_3$, 300 MHz) δ 7.72 (dd, 1H, ph, J=8.5 Hz, J'=1.7 Hz), 7.60 (dd, 1H, ph, J=8.0 Hz, J'=1.8 Hz), 3.92 (m, 6H, —CHCH$_2$NPht, acetal H), 3.61 (s, 3H, —CO$_2$CH$_3$), 3.21 (dd, 1H, —CHCH$_2$NPht, J=8.6 Hz, J=5.8 Hz) 1.44 (s, 3H, —COCH$_3$)

$^{13}$C NMR (CDCl$_3$, 300 MHz) δ 171.2, 167.3, 167.0, 141.1, 134.4, 130.4, 124.9, 124.1, 108.9, 65.4, 65.1, 52.6, 51.8, 37.2, 22.1.

(18) Methyl 3-(5-bromo-1,3-dioxo-1,3-dihydro-isoindol-2-yl)-2-(2-methyl-[1,3]dioxolan-2-yl)propionate Methyl 3-(5-bromo-1,3-dioxo-1,3-dihydro-isoindol-2-yl)-2-(2-methyl-[1,3]dioxolan-2-yl)propionate was prepared (0.48 g, 57 mmol) in the same manner as described in the above example 5 (1) from methyl 3-amino-2-(2-methyl-[1,3]dioxolan-2-yl)propionate (0.62 g, 2.75 mmol) and 4-bromophthalic anhydride (0.62 g, 2.75 mmol), and the obtained product was identified with the following NMR data.

$^1$H NMR (CDCl$_3$, 300 MHz) δ 7.93 (s, 1H, ph), 7.89 (d, 1H, ph, J=1.4 Hz), 7.64 (m, 1H, ph), 3.99–3.87 (m, 6H, acetal, —CHCH$_2$NPht), 3.61 (s, 3H, —CO$_2$CH$_3$), 3.21(m, 1H, —CHCH$_2$NPht), 1.43 (s, 3H, —COCH$_3$)

¹³C NMR (CDCl₃, 300 MHz) δ 171.2, 167.5, 167.1, 137.4, 135.3, 134.0, 133.1, 131.9, 130.9, 129.4, 125.9, 108.9, 65.1, 62.7, 52.6, 37.2, 22.0, 14.3.

(19) Methyl 3-(1,3-dioxo-1,3-dihydro-benzo[e]isoindol-2-yl)-2-(2-methyl-[1,3]dioxolan-2-yl)propionate Methyl 3-(1,3-dioxo-1,3-dihydro-benzo[e]isoindol-2-yl)-2-(2-methyl-[1,3]dioxolan-2-yl)propionate was prepared (0.45 g, 58%) in the same manner as described in the above example 5 (1) from methyl 3-amino-2-(2-methyl-[1,3]dioxolan-2-yl)propionate (0.40 g, 2.11 mmol) and 1,2-naphthalic anhydride (0.55 g, 2.75 mmol), and the obtained product was identified with the following NMR data.

¹H NMR (CDCl₃, 300 MHz) δ 8.77 (d, 1H, ph, J=8.3 Hz), 8.00 (d, 1H, ph, J=8.2 Hz), 7.79 (dd, 1H, ph, J=8.2 Hz, J'=1.2 Hz), 7.57 (d, 1H, ph, J=6.9 Hz), 7.49 (m, 2H, ph), 3.98–3.53 (m, 6H, acetal H, —CHCH₂NPht), 3.53 (s, 3H, —CO₂CH₃), 3.20 (m, 1H, —CHCH₂NPht), 1.39 (s, 3H, —COCH₃)

¹³C NMR (CDCl₃, 300 MHz) δ 171.5, 169.5, 136.9, 135.3, 131.6, 129.1 128.1, 127.8, 125.4, 118.9, 109.1, 65.4, 65.1, 52.6, 52.2, 37.0, 22.1.

(20) Ethyl 3-(5-nitro-1,3-dioxo-1,3-dihydro-isoindol-2-yl)-2-(2-methyl-[1,3]dioxolan-2-yl)propionate Ethyl 3-amino-2-(2-methyl-[1,3]dioxolan-2-yl)propionate (800 mg, 3.94 mmol) was dissolved in 15 mL of chloroform, and 4-nitrophthalic anhydride (988 mg, 4.33 mmol) was added to the obtained solution. The resulting mixture was then refluxed at 80° C. for 5 days. After the reaction was completed, the solvent was evaporated by distilling under a reduced pressure. The residue was purified by performing column chromatography (eluent: n-hexane/ethyl acetate=1/1) to obtain the desired product as a yellow solid (1.24 g, 83%). Rf=0.32 (n-hexane/ethyl acetate=1/1)

¹H NMR (CDCl₃, 300 MHz) δ 8.54 (m, 2H, ph), 7.98 (d, 1H, ph, J=8.0 Hz), 4.08–3.89 (m, 8H, acetal H, —CHCH₂NPht, —OCH₂CH₃), 3.23 (m, 1H, —CHCH₂NPht), 1.43 (s, 3H, CH₃), 1.13 (t, 3H, —OCH₂CH₃, J=7.1 Hz)

¹³C NMR (CDCl₃, 300 MHz) 170.5, 166.2, 165.9, 152.1, 136.8, 133.8, 129.7, 124.9, 119.1, 108.9, 65.4, 65.1, 61.6, 51.8, 37.5, 22.1, 14.5.

(21) Ethyl 3-(4-fluoro-1,3-dioxo-1,3-dihydro-isoindol-2-yl)-2-(2-methyl-[1,3]dioxolan-2-yl)propionate Ethyl 3-(4-fluoro-1,3-dioxo-1,3-dihydro-isoindol-2-yl)-2-(2-methyl-[1,3]dioxolan-2-yl)propionate was prepared (0.25 g, 28%) in the same manner as described in the above example 5 (20) from ethyl 3-amino-2-(2-methyl-[1,3]dioxolan-2-yl)propionate (0.50 g, 2.64 mmol) and 3-fluorophthalic anhydride (0.57 g, 3.43 mmol), and the obtained product was identified with the following NMR data.

¹H NMR (CDCl₃, 300 MHz) δ 7.64 (m, 2H, ph), 7.31 (dd, 1H, ph, J=8.5 Hz, J=0.8 Hz), 4.00 (m, 8H, —CH₂CH₃, acetal H, —CHCH₂NPht), 3.21 (m, 1H, —CHCH₂NPht, J=8.8 Hz, J=5.6 Hz), 1.45 (s, 3H, —COCH₃), 1.13 (t, 3H, —OCH₂CH₃, J=7.1 Hz)

¹³C NMR (CDCl₃, 300 MHz) δ 170.5, 163.8, 155.152.2, 125.5, 125.1, 108.9, 65.3, 65.0, 61.5, 51.6, 37.2, 22.0, 14.3.

(22) Ethyl 3-(4,7-difluoro-1,3-dioxo-1,3-dihydro-isoindol-2-yl)-2-(2-methyl-[1,3]dioxolan-2-yl)propionate Ethyl 3-(4,7-difluoro-1,3-dioxo-1,3-dihydro-isoindol-2-yl)-2-(2-methyl-[1,3]dioxolan-2-yl)propionate was prepared in the same manner as described in the above example 5 (20) from ethyl 3-amino-2-(2-methyl-[1,3]dioxolan-2-yl)propionate (0.80 g, 3.94 mmol) and 3,6-difluorophthalic anhydride (0.94 g, 4.33 mmol), and the obtained product was identified with the following NMR data.

¹H NMR (CDCl₃, 300 MHz) δ 7.96 (dd, 2H, ph, J=5.7 Hz), 4.10 (m, 2H, —OCH₂CH₃), 3.93 (m, 6H, acetal, —CHCH₂NPht), 3.21 (m, 1H, —CHCH₂NPht), 1.45 (s, 3H, —COCH₃), 1.17 (t, 3H, —OCH₂CH₃)

¹³C NMR (CDCl₃, 300 MHz) δ 170.5, 163.8, 155.7, 152.2, 125.5, 125.1, 119.1, 108.9, 65.3, 61.5, 51.6, 37.2, 22.0, 14.3.

(23) Ethyl 3-(4-nitro-1,3-dioxo-1,3-dihydro-isoindol-2-yl)-2-(2-methyl-[1,3]dioxolan-2-yl)propionate Ethyl 3-(4-nitro-1,3-dioxo-1,3-dihydro-isoindol-2-yl)-2-(2-methyl-[1,3]dioxolan-2-yl)propionate was prepared (0.64 g, 51%) in the same manner as described in the above example 5 (20) from ethyl 3-amino-2-(2-methyl-[1,3]dioxolan-2-yl)propionate (0.68 g, 3.34 mmol) and 3-nitrophthalic anhydride (0.84 g, 4.33 mmol), and the obtained product was identified with the following NMR data.

¹H NMR (CDCl₃, 300 MHz) δ 8.05 (d, 2H, ph, J=7.8 Hz), 7.86 (t, 1H, ph, J=7.7 Hz) 4.00 (m, 8H, acetal, —OCH₂CH₃, CHCH₂NPht), 3.23 (dd, 1H, —CHCH₂NPht J=6.5 Hz, J=6.1 Hz), 1.44 (s, 3H, —COCH₃), 1.15 (t, 3H, —OCH₂CH₃, J=7.1 Hz)

¹³C NMR (CDCl₃, 300 MHz) 170.6, 165.8, 163.0, 145.5, 135.8, 134.4, 128.9, 127.5, 124.1, 108.9, 65.4, 65.1, 61.6, 51.6, 37.6, 22.1, 14.4.

(24) Ethyl 3-(4-methyl-1,3-dioxo-1,3-dihydro-isoindol-2-yl)-2-(2-methyl-[1,3]dioxolan-2-yl)propionate Ethyl 3-(4-methyl-1,3-dioxo-1,3-dihydro-isoindol-2-yl)-2-(2-methyl-[1,3]dioxolan-2-yl)propionate was prepared (0.57 g, 76%) in the same manner as described in the above example 5 (20) from ethyl 3-amino-2-(2-methyl-[1,3]dioxolan-2-yl)propionate (0.60 g, 3.25 mmol) and 3-methylphthalic anhydride (0.79 g, 4.87 mmol), and the obtained product was identified with the following NMR data.

¹H NMR (CDCl₃, 300 MHz) δ 7.57 (d, 1H, ph, J=6.9 Hz), 7.47 (t, 1H, ph, J=7.5 Hz), 7.37 (d, 1H, ph, J=7.4 Hz), 4.08–3.88 (m, 8H, acetal H, —CHCH₂NPht, —OCH₂CH₃), 3.21 (m, 1H, —CHCH₂NPht), 2.60 (s, 3H, CH₃), 1.45 (s, 3H, CH₃), 1.09 (t, 3H, —OCH₂CH₃, J=7.1 Hz)

¹³C NMR (CDCl₃, 300 MHz) δ 170.9, 169.1, 168.3, 138.3, 136.7, 135.5, 133.8, 132.8, 121.3, 109.1, 65.1, 61.4, 52.1, 36.9, 22.1, 17.9, 14.3.

(25) Ethyl 3-(5-methyl-1,3-dioxo-1,3-dihydro-isoindol-2-yl)-2-(2-methyl-[1,3]dioxolan-2-yl)propionate Ethyl 3-(5-methyl-1,3-dioxo-1,3-dihydro-isoindol-2-yl)-2-(2-methyl-[1,3]dioxolan-2-yl)propionate was prepared (0.38 g, 40%) in the same manner as described in the above example 5 (20) from ethyl 3-amino-2-(2-methyl-[1,3]dioxolan-2-yl)propionate (0.60 g, 3.25 mmol) and 4-methylphthalic anhydride (0.79 g, 4.87 mmol), and the obtained product was identified with the following NMR data.

¹H NMR (CDCl₃, 300 MHz) δ 7.62 (d, 1H, ph, J=7.6 Hz), 7.53 (s, 1H, ph), 7.42 (d, 1H, ph, J=7.6 Hz), 4.08–3.85 (m, 8H, acetal H, —CHCH₂NPht, —OCH₂CH₃), 3.20 (m, 1H, —CHCH₂NPht), 2.42 (s, 3H, CH₃), 1.43 (s, 3H, CH₃), 1.08 (t, 3H, —OCH₂CH₃, J=7.1 Hz)

¹³C NMR (CDCl₃, 300 MHz) δ 172.8, 169.1, 168.3, 145.6, 134.6, 132.7, 131.5, 131.2, 130.5, 124.2, 123.6, 109.1, 65.3, 62.2, 61.4, 51.9, 36.9, 21.8, 21.7, 14.6.

(26) Ethyl 3-(5-t-butyl-1,3-dioxo-1,3-dihydro-isoindol-2-yl)-2-(2-methyl-[1,3]dioxolan-2-yl)propionate Ethyl 3-(5-t-butyl-1,3-dioxo-1,3-dihydro-isoindol-2-yl)-2-(2-methyl-[1,3]dioxolan-2-yl)propionate was prepared (0.54 g, 35%) in the same manner as described in the above example 5 (20) from ethyl 3-amino-2-(2-methyl-[1,3]dioxolan-2-yl)propionate (0.80 g, 3.94 mmol) and 4-t-butylphthalic anhydride (0.88 g, 4.33 mmol), and the obtained product was identified with the following NMR data.

¹H NMR (CDCl₃, 300 MHz) δ 7.78 (s, 1H, ph), 7.64 (dd, 2H, ph, J=12.8 Hz, J=1.3 Hz), 4.07–3.87 (m, 8H, acetal H, —CHCH$_2$NPht, —OCH$_2$CH$_3$), 3.21(m, 1H, —CHCH$_2$NPht), 1.44 (s, 3H, CH$_3$), 1.29 (s, 9H, C(CH$_3$)$_3$), 1.10 (t, 3H, —OCH$_2$CH$_3$, J=7.1 Hz)

$^{13}$C NMR (CDCl$_3$, 300 MHz) 170.8, 168.7, 158.9, 132.6, 131.3, 129.7, 123.4, 120.8, 109.0, 65.3, 65.1, 31.3, 51.9, 36.9, 36.1, 31.5, 22.1, 14.4.

(27) Ethyl 3-(4-hydroxy-1,3-dioxo-1,3-dihydro-isoindol-2-yl)-2-(2-methyl-[1,3]dioxolan-2-yl)propionate Ethyl 3-(4-hydroxy-1,3-dioxo-1,3-dihydro-isoindol-2-yl)-2-(2-methyl-[1,3]dioxolan-2-yl)propionate was prepared (0.46 g, 67%) in the same manner as described in the above example 5 (20) from ethyl 3-amino-2-(2-methyl-[1,3]dioxolan-2-yl)propionate (0.40 g, 1.96 mmol) and 3-hydroxyphthalic anhydride (0.42 g, 2.16 mmol), and the obtained product was identified with the following NMR data.

$^1$H NMR (CDCl$_3$, 300 MHz) δ 7.50 (dd, 1H, ph, J=8.3 Hz, J'=7.3 Hz), 7.29 (d, 1H, ph, J=7.2 Hz), 7.08 (d, 1H, ph, J=8.3 Hz), 3.96 (m, 8H, OCH$_2$CH$_3$, acetal, —CHCH$_2$NPht, 3.21 (dd, 1H, —CHCH$_2$NPht, J=9.1 Hz, J'=2.3 Hz), 1.44 (s, 3H, —COCH$_3$), 1.12 (t, 3H, —OCH$_2$CH$_3$, J=7.1 Hz)

$^{13}$C NMR (CDCl$_3$, 300 MHz) 170.8, 170.4, 167.9, 155.1, 136.8, 132.4, 123.1, 116.4, 108.9, 65.3, 65.1, 61.5, 52.0, 36.8, 22.1, 14.4.

(28) Ethyl 3-(4,7-dichloro-1,3-dioxo-1,3-dihydro-isoindol-2-yl)-2-(2-methyl-[1,3]dioxolan-2-yl)propionate Ethyl 3-(4,7-dichloro-1,3-dioxo-1,3-dihydro-isoindol-2-yl)-2-(2-methyl-[1,3]dioxolan-2-yl)propionate was prepared (1.10 g, 74%) in the same manner as described in the above example 5 (20) from ethyl 3-amino-2-(2-methyl-[1,3]dioxolan-2-yl)propionate (0.80 g, 3.94 mmol) and 3,6-dichlorophthalic anhydride (0.94 g, 4.33 mmol), and the obtained product was identified with the following NMR data.

$^1$H NMR (CDCl$_3$, 300 MHz) δ 7.65 (s, 2H, ph), 3.91–3.74 (m, 8H, acetal H, —CHCH$_2$NPht, —OCH$_2$CH$_3$), 3.04 (m, 1H, —CHCH$_2$NPht), 1.26 (s, 3H, CH$_3$), 0.98 (t, 3H, —OCH$_2$CH$_3$, J=7.1 Hz)

$^{13}$C NMR (CDCl$_3$, 300 MHz) δ 200.3, 170.2, 167.6, 165.8, 139.0, 131.4, 125.5, 108.8, 65.1, 62.1, 60.4, 57.1, 51.5, 37.2, 28.9, 21.8, 14.4.

(29) Ethyl 3-(5,6-dichloro-1,3-dioxo-1,3-dihydro-isoindol-2-yl)-2-(2-methyl-[1,3]dioxolan-2-yl)propionate Ethyl 3-(5,6-dichloro-1,3-dioxo-1,3-dihydro-isoindol-2-yl)-2-(2-methyl-[1,3]dioxolan-2-yl)propionate was prepared (0.66 g, 50%) in the same manner as described in the above example 5 (20) from ethyl 3-amino-2-(2-methyl-[1,3]dioxolan-2-yl)propionate (0.60 g, 3.25 mmol) and 4,5-dichlorophthalic anhydride (0.85 g, 3.90 mmol), and the obtained product was identified with the following NMR data.

$^1$H NMR (CDCl$_3$, 300 MHz) δ 7.87 (s, 2H, ph), 4.07–3.88 (m, 8H, acetal H, —CHCH$_2$NPht, —OCH$_2$CH$_3$), 3.20 (m, 1H, —CHCH$_2$NPht), 1.42 (s, 3H, CH$_3$), 1.14 (t, 3H, —OCH$_2$CH$_3$, J=7.1 Hz)

$^{13}$C NMR (CDCl$_3$, 300 MHz) 170.6, 166.3, 139.3, 135.8, 131.5, 131.2, 125.8, 109.0, 65.1, 62.8, 61.5, 51.8, 37.4, 22.1, 14.4, 14.3.

(30) Ethyl 3-(1,3-dioxo-4-phenyl-1,3-dihydro-benzo[f]isoindol-2-yl)-2-(2-methyl-[1,3]dioxolan-2-yl)propionate Ethyl 3-(1,3-dioxo-4-phenyl-1,3-dihydro-benzo[f]isoindol-2-yl)-2-(2-methyl-[1,3]dioxolan-2-yl)propionate was prepared (1.12 g, 62%) in the same manner as described in the above example 5 (20) from ethyl 3-amino-2-(2-methyl-[1,3]dioxolan-2-yl)propionate (0.80 g, 3.93 mmol) and 1-phenyl-2,3-naphthalic anhydride (1.19 g, 3.93 mmol), and the obtained product was identified with the following NMR data.

$^1$H NMR (CDCl$_3$, 300 Mz) δ 8.28 (s, 1H, ph), 7.98 (d, 1H, ph), 7.70 d, 1H. ph), 7.60 (t, 1H, ph), 7.44 (m, 4H. ph), 7.31 (m, 2H, ph), 4.05–3.81 (m, 8H, acetal, —CHCH$_2$NPht, —OCH$_2$CH$_3$), 3.23 (m, 1H, —CHCH$_2$NPht), 1.42 (s, 3H, —COCH$_3$), 1.07(t, 3H, —OCH$_2$CH$_3$)

$^{13}$C NMR (CDCl$_3$, 300 MHz) 170.8, 167.7, 140.6, 135.8, 134.8, 130.7, 130.3, 130.2, 129.5, 128.9, 128.6, 124.6, 124.1, 109.0, 65.3, 65.1, 61.3, 51.7, 37.2, 22.1, 14.4.

(31) Ethyl 3-(1,3-dioxo-1,3,4,5,6,7-hexahydro-isoindol-2-yl)-2-(2-methyl-[1,3]dioxolan-2-yl)propionate Ethyl 3-(1,3-dioxo-1,3,4,5,6,7-hexahydro-isoindol-2-yl)-2-(2-methyl-[1,3]dioxolan-2-yl)propionate was prepared (0.91 g, 69%) in the same manner as described in the above example 5 (20) from ethyl 3-amino-2-(2-methyl-[1,3]dioxolan-2-yl)propionate (0.80 g, 3.94 mmol) and 3,4,5,6-tetrahydrophthalic anhydride (0.78 g, 4.33 mmol), and the obtained product was identified with the following NMR data.

$^1$H NMR (CDCl$_3$, 300 MHz) δ 4.12 (q, 2H, —OCH$_2$CH$_3$, J=6.1 OCH2CH3, J=6.1 acetal), 3.88 (dd, 1H, —CHCH$_2$NPht J=12.2 Hz, J'=4.5 Hz), 3.74 (dd, 1H, —CHCH$_2$NPht J=12.2 Hz, J'=4.5 Hz), 3.12 (m, 1H, —CHCH$_2$NPht), 2.28 (s, 4H, cyclohexane), 1.71 (s, 4H, cyclohexane), 1.46 (s, 3H, —COCH$_3$), 1.2 (t, 3H, —OCH$_2$CH$_3$)

$^{13}$C NMR (CDCl$_3$, 300 MHz) 171.1, 170.9, 141.9, 108.9, 65.2, 65.0, 61.3, 52.4, 36.6, 22.1, 21.7, 20.3, 14.4.

(32) Ethyl 3-(2,5-dioxo-3-phenyl-2,5-dihydro-pyrrol-1-yl)-2-(2-methyl-[1,3]dioxolan-2-yl)propionate Ethyl 3-(2,5-dioxo-3-phenyl-2,5-dihydro-pyrrol-1-yl)-2-(2-methyl-[1,3]dioxolan-2-yl)propionate was prepared (0.41 g, 58%) in the same manner as described in the above example 5 (20) from ethyl 3-amino-2-(2-methyl-[1,3]dioxolan-2-yl)propionate (0.40 g, 1.96 mmol) and phenylmaleic anhydride (0.57 g, 2.16 mmol), and the obtained product was identified with the following NMR data.

$^1$H NMR (CDCl$_3$, 300 MHz) δ 7.84 (m, 2H, ph), 7.38 (m, 3H, ph), 6.65 (s, 1H, =CH), 4.08–3.82 (m, 8H, acetal H, —CHCH$_2$NPht, —OCH$_2$CH$_3$), 3.20 (m, 1H, —CHCH2NPht), 1.43 (s, 3H, CH$_3$), 1.15(t, 3H, —OCH$_2$CH$_3$, J=7.1 Hz)

$^{13}$C NMR (CDCl$_3$, 300 MHz) 175.9, 170.8, 170.2, 144.2, 131.5, 131.4, 129.3, 129.3, 129.1, 128.9, 128.7, 124.3, 109.2, 109.0, 65.1, 64.9, 52.0, 40.5, 22.0, 14.5.

(33) Ethyl 3-(2,5-dioxo-3,4-diphenyl-2,5-dihydro-pyrrol-1-yl)-2-(2-methyl-[1,3]dioxolan-2-yl)propionate Ethyl 3-(2,5-dioxo-3,4-diphenyl-2,5-dihydro-pyrrol-1-yl)-2-(2-methyl-[1,3]dioxolan-2-yl)propionate was prepared (1.00 g, 61%) in the same manner as described in the above example 5 (20) from ethyl 3-amino-2-(2-methyl-[1,3]dioxolan-2-yl)propionate (0.80 g, 3.94 mmol) and 1,2-diphenylmaleic anhydride (1.10 g, 4.33 mmol), and the obtained product was identified with the following NMR data.

$^1$H NMR (CDCl$_3$, 300 MHz) δ 7.39 (m, 4H, ph), 7.28 (m, 6H, ph), 7.09 (q, 2H, —OCH$_2$CH$_3$, J=7.1 Hz), 3.93 (m, 6H, acetal, —CHCH$_2$NPht), 3.21 (m, 1H, —CHCH$_2$NPht), 1.45 (s, 3H, —COCH$_3$), 1.17 (t, 3H, —OCH$_2$CH$_3$, J=7.1 Hz)

$^{13}$C NMR (CDCl$_3$, 300 MHz) 170.9, 170.7, 136.6, 130.2, 128.9, 109.0, 65.3, 65.1, 61.4, 52.0, 37.4, 22.1, 14.5.

(34) Ethyl 3-(5-fluoro-1,3-dioxo-1,3-dihydro-isoindol-2-yl)-2-(2-methyl-[1,3]dioxolan-2-yl)propionate Ethyl 3-(5-fluoro-1,3-dioxo-1,3-dihydro-isoindol-2-yl)-2-(2-methyl-[1,3]dioxolan-2-yl)propionate was prepared (0.77 g, 56%) in the same manner as described in the above example 5 (20) from ethyl 3-amino-2-(2-methyl-[1,3]dioxolan-2-yl)propionate (0.80 g, 3.94 mmol) and 4-fluorophthalic anhydride (0.78 g, 4.72 mmol), and the obtained product was identified with the following NMR data.

¹H NMR (CDCl₃, 300 MHz) δ 7.76 (dd, 1H, ph, J=5.8 Hz, J'=4.5 Hz), 7.41 (dd, 1H, ph, J=7.1 Hz, J'=2.2 Hz), 7.31 (ddd, 1H, ph, J=9.0 Hz, J'=9.3 Hz, J"=2.3 Hz), 3.99 (m, 8H, acetal, —CHCH₂NPht, —OCH₂CH₃), 3.19 (dd, 1H, —CHCH₂NPht, J=8.9 Hz, J'=5.5 Hz), 1.41 (s, 3H, —COCH₃), 1.09 (t, 3H, —OCH₂CH₃, J=7.1 Hz)

¹³C NMR (CDCl₃, 300 MHz) 170.6, 168.4, 167.1, 166.8, 135.2, 165.0, 128.1, 125.9, 111.5, 111.2, 65.2, 65.0, 61.3, 51.8, 37.1, 21.9, 14.3.

(35) Ethyl 3-(5-chloro-1,3-dioxo-1,3-dihydro-isoindol-2-yl)-2-(2-methyl-[1,3]dioxolan-2-yl)propionate Ethyl 3-(5-chloro-1,3-dioxo-1,3-dihydro-isoindol-2-yl)-2-(2-methyl-[1,3]dioxolan-2-yl)propionate was prepared (0.37 g, 50%) in the same manner as described in the above example 5 (20) from ethyl 3-amino-2-(2-methyl-[1,3]dioxolan-2-yl)propionate (0.40 g, 1.97 mmol) and 4-chlorophthalic anhydride (0.47 g, 2.56 mmol), and the obtained product was identified with the following NMR data.

¹H NMR (CDCl₃, 300 MHz) δ 7.72 (dd, 2H, ph, J=8.6 Hz, J=1.5 Hz), 7.60 (dd, 1H, ph, J=7.9 Hz, J=1.8 Hz), 3.93 (m, 8H, acetal, —CHCH₂NPht, —OCH₂CH₃), 3.21 (dd, 1H, —CHCH2NPht J=8.8 Hz, J=5.6 Hz), 1.44 (s, 3H, —COCH3), 1.12 (t, 3H, —OCH₂CH₃, J=7.1 Hz)

¹³C NMR (CDCl₃, 300 MHz) 170.6, 167.3, 141.1, 134.4, 130.5, 124.9, 109.0, 65.3, 61.4, 51.8, 37.2, 22.1, 14.4.

(36) Ethyl 3-(5-bromo-1,3-dioxo-1,3-dihydro-isoindol-2-yl)-2-(2-methyl-[1,3]dioxolan-2-yl)propionate Ethyl 3-(5-bromo-1,3-dioxo-1,3-dihydro-isoindol-2-yl)-2-(2-methyl-[1,3]dioxolan-2-yl)propionate was prepared (0.42 g, 52%) in the same manner as described in the above example 5 (20) from ethyl 3-amino-2-(2-methyl-[1,3]dioxolan-2-yl)propionate (0.40 g, 1.97 mmol) and 4-bromophthalic anhydride (0.58 g, 2.56 mmol), and the obtained product was identified with the following NMR data.

¹H NMR (CDCl₃, 300 MHz) δ 7.76 (dd, 1H, ph, J=8.2 Hz, J=4.5 Hz), 7.41 (dd, 1H, ph, J=7.0 Hz, J=2.2 Hz), 7.32 (t, 1H, ph, J=9.7 Hz), 4.07–3.87 (m, 8H, acetal, —CHCH₂NPht, —OCH₂CH₃), 3.91 (dd, 1H, —CHCH₂NPht, J=8.9 Hz, J=5.5 Hz), 1.42 (s, 3H, —COCH₃), 1.09 (t, 3H, —OCH₂CH₃, J=7.1 Hz)

¹³C NMR (CDCl₃, 300 MHz) 170.6, 168.4, 167.1, 166.8, 135.1, 135.0, 128.1, 126.0, 125.9, 121.5, 111.5, 108.9, 65.2, 61.3, 51.8, 37.1, 21.9, 14.3.

(37) Ethyl 3-(1,3-dioxo-1,3-dihydro-benzo[e]isoindol-2-yl)-2-(2-methyl-[1,3]dioxolan-2-yl)propionate Ethyl 3-(1,3-dioxo-1,3-dihydro-benzo[e]isoindol-2-yl)-2-(2-methyl-[1,3]dioxolan-2-yl)propionate was prepared (0.55 g, 73%) in the same manner as described in the above example 5 (20) from ethyl 3-amino-2-(2-methyl-[1,3]dioxolan-2-yl)propionate (0.40 g, 1.97 mmol) and 1,2-naphthalic anhydride (0.51 g, 2.56 mmol), and the obtained product was identified with the following NMR data.

¹H NMR (CDCl₃, 300 MHz) δ 8.87 (dd, 1H, ph, J=8.4 Hz, J=0.4 Hz), 8.08 (d, 1H, ph, J=8.3 Hz), 7.80 (d, 1H, ph, J=7.7 Hz), 7.76 (d, 1H, ph, J=8.2 Hz), 7.62 (m, 2H, ph), 4.09–3.90 (m, 8H, acetal H, —CHCH₂NPht, —OCH₂CH₃), 3.27 (m, 1H, —CHCH₂NPht) 1.48 (s, 3H, —CH₃), 1.09 (t, 3H, —OCH₂CH₃, J=7.1 Hz)

¹³C NMR (CDCl₃, 300 MHz) δ 170.3, 169.5, 168.9, 136.9, 135.3, 131.6, 129.9, 129.1, 129.0, 127.7, 118.8, 109.1, 65.3, 65.1, 52.1, 37.0, 22.1, 14.4

(38) Allyl 3-(4-fluoro-1,3-dioxo-1,3-dihydro-isoindol-2-yl)-2-(2-methyl-[1,3]dioxolan-2-yl)propionate Allyl 3-amino-2-(2-methyl-[1,3]dioxolan-2-yl)propionate (400 mg, 1.86 mmol) was dissolved in 10 mL of chloroform, and 3-fluorophthalic anhydride (401 mg, 2.42 mol) was added to the obtained solution. The resulting mixture was then refluxed at 80° C. for 3 days after adding. After the reaction was completed, the solvent was evaporated by distilling under a reduced pressure. The residue was purified by performing column chromatography (eluent: n-hexane/ethyl acetate=3/1) to obtain the desired product as a white solid (351 mg, 52%). Rf=0.29 (eluent: n-hexane/ethyl acetate=2/1)

¹H NMR (CDCl₃, 300 MHz) δ 7.62 (m, 2H, ph), 7.32 (t, 1H, ph, J=7.8 Hz), 5.80 (m, 1H, —CH₂CH=CH₂), 5.22 (d, 1H, —CH₂CH=CH₂, J=10.0 Hz), 5.07 (d, 1H, —CH₂CH=CH₂, J=9.0 Hz), 4.51 (d, 1H, CH₂CH=CH₂, J=5.9 Hz), 4.01–3.89 (m, 6H, acetal H, —CHCH₂NPht), 3.55 (m, 1H, —CHCH₂NPht), 1.45 (s, 3H, —COCH₃)

¹³C NMR (CDCl₃, 300 MHz) δ 170.4, 165.0, 137.1, 132.1, 122.9, 119.9, 108.9, 66.1, 65.3, 51.8, 37.1, 22.1.

(39) Allyl 3-(4,7-difluoro-1,3-dioxo-1,3-dihydro-isoindol-2-yl)-2-(2-methyl-[1,3]dioxolan-2-yl)propionate Allyl 3-amino-2-(2-methyl-[1,3]dioxolan-2-yl)propionate (400 mg, 1.86 mmol) was dissolved in 10 mL of chloroform, and 4,7-difluorophthalic anhydride (445 mg, 2.42 mol) was then added to the obtained solution. The resulting mixture was then refluxed at 80° C. for 3 days. After the reaction was completed, the solvent was evaporated by distilling under a reduced pressure. The residue was purified by performing column chromatography (eluent: n-hexane/ethyl acetate=3/1) to obtain the desired product as an oil (369 mg, 52%). Rf=0.34 (eluent: n-hexane/ethyl acetate=2/1)

¹H NMR (CDCl₃, 300 MHz) δ 7.30 (t, 2H, J=5.6 Hz, ph), 5.79 (m, 1H, —CH₂CH=CH₂), 5.22 (dd, 1H, —CH₂CH=CH₂, J=1.46 Hz, J=17.2 Hz), 5.10 (dd, 1H, —CH₂CH=CH₂, J=1.1 Hz. J=10.4 Hz), 4.52 (d, 1H, CH₂CH=CH₂, J=5.8 Hz), 3.93 (m, 6H, acetal H, —CHCH₂NPht), 3.23 (m, 1H, —CHCH₂NPht), 1.44 (s, 3H, —COCH₃)

¹³C NMR (CDCl₃, 300 MHz) δ 170.3, 163.9, 154.0, 132.1, 125.2, 119.0, 108.9, 66.2, 65.3, 65.1, 51.6, 37.2, 22.1.

Example 6

Preparation of Compound (VI)

(1) Methyl 2-(4-hydroxy-1,3-dioxo-1,3-dihydro-isoindol-2-ylmethyl)-3-oxo-butyrate Methyl 3-(4-hydroxy-1,3-dioxo-1,3-dihydro-isoindol-2-yl)-2-(2-methyl-[1,3]dioxolan-2-yl)propionate (0.84 g, 2.51 mmol) was dissolved in 24 mL of a solvent mixture of acetone/water (v/v=5/1), and p-toluenesulfonic acid monohydrate (about 0.19 g) was then added to the obtained solution. The resulting mixture was refluxed at 100° C. for 2 days. After the reaction was completed, the reaction mixture was concentrated under a reduced pressure and then extracted with dichloromethane. The desired product was obtained (0.55 mg, 75%) by performing column chromatography (eluent: n-hexane/ethyl acetate=2/1).

¹H NMR (CDCl₃, 300 MHz) δ 7.52 (dd, 1H, ph, J=7.5 Hz, J'=7.3 Hz), 7.29 (d, 1H, ph, J'=7.2 Hz), 7.09 (d, 1H, ph, J=3.70 Hz) 4.08 (m, 2H, —CHCH₂NPht), 3.97 (dd, 1H, —CHCH₂NPht, J=8.3 Hz, J'=6.3 Hz), 3.68 (s, 3H —CO₂CH₃), 1.43 (s, 3H, —COCH₃)

¹³C NMR (CDCl₃, 300 MHz) δ 200.7, 170.1, 168.4, 167.8, 155.1, 136.9, 132.1, 123.3, 116.6, 114.7, 57.5, 53.3, 36.2, 29.4.

(2) Methyl 2-(4-fluoro-1,3-dioxo-1,3-dihydro-isoindol-2-ylmethyl)-3-oxo-butyrate Methyl 2-(4-fluoro-1,3-dioxo-1,3-dihydro-isoindol-2-ylmethyl)-3-oxo-butyrate was prepared (71 mg, 34%) in the same manner as described in the above example 6 (1) from methyl 3-(4-fluoro-1,3-dioxo-1,3-dihydro-isoindol-2-yl)-2-(2-methyl-[1,3]dioxolan-2-yl)propionate (0.23 g, 0.70 mmol) and p-toluenesulfonic acid monohydrate (20 mg), and the obtained product was identified with the following NMR data.

$^1$H NMR (CDCl$_3$, 300 MHz) δ 7.61 (m, 2H, ph), 7.30 (t, 1H, ph, J=8.9 Hz), 4.05–3.88 (m, 6H, acetal H, —CHCH$_2$NPht), 3.61 (s, 3H, —CO$_2$CH$_3$) 3.22 (m, 1H, —CHCH$_2$NPht), 1.44 (s, 3H, —COCH$_3$)

$^{13}$C NMR (CDCl$_3$, 300 MHz) δ 206.1, 168.4, 165.2, 159.6, 156.1, 137.3, 134.6, 123.1, 122.9, 122.8, 120.7, 120.1, 119.9, 118.0, 57.4, 41.7, 36.4, 33.5.

(3) Methyl 2-(4,7-difluoro-1,3-dioxo-1,3-dihydro-isoindol-2-ylmethyl)-3-oxo-butyrate Methyl 2-(4,7-difluoro-1,3-dioxo-1,3-dihydro-isoindol-2-ylmethyl)-3-oxo-butyrate was prepared (46 mg, 19%) in the same manner as described in the above example 6 (1) from methyl 3-(4,7-difluoro-1,3-dioxo-1,3-dihydro-isoindol-2-yl)-2-(2-methyl-[1,3]dioxolan-2-yl)propionate (0.24 g, 0.67 mmol) and p-toluenesulfonic acid monohydrate (51 mg), and the obtained product was identified with the following NMR data.

$^1$H NMR (CDCl$_3$, 300 MHz) δ 7.33 (t, 2H, ph, J=5.3 Hz), 4.08 (m, 2H, —CHCH$_2$NPht), 3.93 (d, 1H, —CHCH$_2$NPht, J=6.7 Hz), 3.69 (s, 3H —CO$_2$CH$_3$), 2.23 (s, 3H, —COCH$_3$)

$^{13}$C NMR (CDCl$_3$, 300 MHz) δ 200.5, 178.1, 173.0. 168.3, 163.9, 155.8, 152.3, 125.7, 118.9, 95.6, 57.2, 53.5, 36.5, 35.9, 29.3, 19.7.

(4) Methyl 2-(4-nitro-1,3-dioxo-1,3-dihydro-isoindol-2-ylmethyl)-3-oxo-butyrate

Methyl 2-(4-nitro-1,3-dioxo-1,3-dihydro-isoindol-2-ylmethyl)-3-oxo-butyrate was prepared in the same manner as described in the above example 6 (1) from methyl 3-(4-nitro-1,3-dioxo-1,3-dihydro-isoindol-2-yl)-2-(2-methyl-[1, 3]dioxolan-2-yl)propionate (0.24 g, 0.67 mmol) and p-toluenesulfonic acid monohydrate (51 mg), and the obtained product was identified with the following NMR data.

$^1$H NMR (CDCl$_3$, 300 MHz) δ 8.06 (m, 2H, ph), 7.87 (t, 1H, ph, J=7.8 Hz), 4.14 (dd, 2H, —CHCH$_2$NPht, J=12.0 Hz, J'=5.8 Hz), 3.96 (t, 1H, —CHCH$_2$NPht, J=6.4 Hz), 3.68 (s, 3H, —CO$_2$CH$_3$, 2.23 (s, 3H, —COCH$_3$)

$^{13}$C NMR (CDCl$_3$, 300 MHz) δ 200.5, 168.3, 165.6, 162.9, 145.5, 136.0, 134.2, 129.2, 127.7, 123.9, 57.1, 53.4, 36.9, 29.4, 22.1.

(5) Methyl 2-(5-nitro-1,3-dioxo-1,3-dihydro-isoindol-2-ylmethyl)-3-oxo-butyrate

Methyl 2-(5-nitro-1,3-dioxo-1,3-dihydro-isoindol-2-ylmethyl)-3-oxo-butyrate was prepared (95 mg, 35%) in the same manner as described in the above example 6 (1) from methyl 3-(5-nitro-1,3-dioxo-1,3-dihydro-isoindol-2-yl)-2-(2-methyl-[1,3]dioxolan-2-yl)propionate (0.29 g, 0.82 mmol) and p-toluenesulfonic acid monohydrate (50 mg), and the obtained product was identified with the following NMR data.

$^1$H NMR (CDCl$_3$, 300 MHz) δ 8.55 (m, 2H, ph), 7.98 (d, 1H, ph, J=5.1 Hz), 4.15 (m, 2H, —CHCH$_2$NPht), 3.97 (m, 1H, —CHCH$_2$NPht), 3.68 (s, 3H, —CO$_2$CH$_3$), 2.23 (s, 3H, —COCH$_3$)

$^{13}$C NMR (CDCl$_3$, 300 MHz) δ 200.4, 168.2, 166.1, 152.3, 136.6, 129.6, 125.1, 119.3, 91.3, 57.1, 53.4, 36.9, 29.4.

(6) Methyl 2-(4-methyl-1,3-dioxo-1,3-dihydro-isoindol-2-ylmethyl)-3-oxo-butyrate Methyl 2-(4-methyl-1,3-dioxo-1,3-dihydro-isoindol-2-ylmethyl)-3-oxo-butyrate was prepared (117 mg, 31%) in the same manner as described in the above example 6 (1) from methyl 3-(4-methyl-1,3-dioxo-1,3-dihydro-isoindol-2-yl)-2-(2-methyl-[1,3]dioxolan-2-yl)propionate (0.37 g, 1.31 mmol) and p-toluenesulfonic acid monohydrate (51 mg), and the obtained product was identified with the following NMR data.

$^1$H NMR (CDCl$_3$, 300 MHz) δ 7.57 (d, 1H, ph, J=7.2 Hz), 7.49 (t, 1H, ph, J=7.6 Hz), 7.38 (d, 1H, ph, J=7.6 Hz), 4.10 (m, 2H, —CHCH$_2$NPht), 3.95 (dd, 1H, —CHCH$_2$NPht J=8.1 Hz, J'=6.6 Hz), 3.67 (s, 3H, —CO$_2$CH$_3$), 2.60 (s, 3H, CH$_3$), 2.22 (s, 3H, COCH$_3$)

$^{13}$C NMR (CDCl$_3$, 300 MHz) δ 200.9, 168.9, 168.5, 138.5, 136.9, 134.0, 132.6, 128.9, 121.5, 57.8, 57.7, 53.2, 36.1, 29.3, 17.9.

(7) Methyl 2-(5-methyl-1,3-dioxo-1,3-dihydro-isoindol-2-ylmethyl)-3-oxo-butyrate Methyl 2-(5-methyl-1,3-dioxo-1,3-dihydro-isoindol-2-ylmethyl)-3-oxo-butyrate was prepared (23 mg, 26%) in the same manner as described in the above example 6 (1) from methyl 3-(5-methyl-1,3-dioxo-1,3-dihydro-isoindol-2-yl)-2-(2-methyl-[1,3]dioxolan-2-yl)propionate (0.10 g, 0.30 mmol) and p-toluenesulfonic acid monohydrate (10 mg), and the obtained product was identified with the following NMR data.

$^1$H NMR (CDCl$_3$, 300 MHz) δ 7.63 (d, 1H, ph, J=7.6 Hz), 7.56 (s, 1H, ph), 7.43 (d, 1H, ph, J=7.7 Hz) 4.09 (m, 2H, —CHCH$_2$NPht), 3.95 (dd, 1H, —CHCH$_2$NPht J=8.3 Hz, J'=6.5 Hz), 3.66 (s, 3H, —CO$_2$CH$_3$), 2.50 (s, 3H, —CH$_3$), 2.21 (s, 3H, —COCH$_3$)

$^{13}$C NMR (CDCl$_3$, 300 MHz) δ 200.9, 168.5, 168.4, 168.3, 145.9, 135.1, 132.5, 129.7, 124.4, 123.7, 57.69, 53.3, 36.3, 29.4, 36.3, 29.4, 22.4.

(8) Methyl 2-(5-t-butyl-1,3-dioxo-1,3-dihydro-isoindol-2-ylmethyl)-3-oxo-butyrate Methyl 2-(5-t-butyl-1,3-dioxo-1,3-dihydro-isoindol-2-ylmethyl)-3-oxo-butyrate was prepared (42 mg, 34%) in the same manner as described in the above example 6 (1) from methyl 3-(5-t-butyl-1,3-dioxo-1,3-dihydro-isoindol-2-yl)-2-(2-methyl-[1,3]dioxolan-2-yl)propionate (0.14 g, 0.34 mmol) and p-toluenesulfonic acid monohydrate (13 mg), and the obtained product was identified with the following NMR data.

$^1$H NMR (CDCl$_3$, 300 MHz) δ 7.79 (s, 1H, ph), 7.66 (m, 2H, ph), 3.87 (dd, 2H, —CHCH$_2$NPht, J=7.5 Hz, J=7.2 Hz), 3.67 (s, 3H, —CO$_2$CH$_3$), 2.79 (dd, 1H, —CHCH$_2$NPht, J=7.5 Hz, J=6.5 Hz), 2.23 (s, 3H, —CO$_2$CH$_3$), 1.29 (s, 3H, —C(CH$_3$)$_3$)

$^{13}$C NMR (CDCl$_3$, 300 MHz) δ 206.2, 200.8, 168.9, 159.2, 132.6, 132.4, 129.7, 123.6, 121.0, 57.4, 53.2, 42.0, 36.3, 36.1, 33.3, 31.5, 30.3, 29.3.

(9) Methyl 2-(4,7-dichloro-1,3-dioxo-1,3-dihydro-isoindol-2-ylmethyl)-3-oxo-butyrate Methyl 2-(4,7-dichloro-1,3-dioxo-1,3-dihydro-isoindol-2-ylmethyl)-3-oxo-butyrate was prepared (69 mg, 39%) in the same manner as described in the above example 6 (1) from methyl 3-(4,7-dichloro-1,3-dioxo-1,3-dihydro-isoindol-2-yl)-2-(2-methyl-[1,3]dioxolan-2-yl)propionate (0.20 g, 0.52 mmol) and p-toluenesulfonic acid monohydrate (50 mg), and the obtained product was identified with the following NMR data.

$^1$H NMR (CDCl$_3$, 300 MHz) δ 7.49 (s, 2H, ph), 4.10 (m, 2H, —CHCH$_2$NPht), 3.95 (m, 2H, —CHCH$_2$NPht), 3.69 (s, 3H, —CO$_2$CH$_3$), 2.23 (s, 3H, —COCH$_3$)

$^{13}$C NMR (CDCl$_3$, 300 MHz) δ 200.6, 168.3, 164.4, 137.1, 136.9, 130.5, 129.4, 57.3, 53.4, 36.5, 29.3.

(10) Methyl 2-(5,6-dichloro-1,3-dioxo-1,3-dihydro-isoindol-2-ylmethyl)-3-oxo-butyrate Methyl 2-(5,6-dichloro-1,3-dioxo-1,3-dihydro-isoindol-2-ylmethyl)-3-oxo-butyrate was prepared (46 mg, 19%) in the same manner as described in the above example 6 (1) from methyl 3-(5,6-dichloro-1,3-dioxo-1,3-dihydro-isoindol-2-yl)-2-(2-methyl-[1,3]dioxolan-2-yl)propionate (0.24 g, 0.67 mmol) and p-toluenesulfonic acid monohydrate (51 mg), and the obtained product was identified with the following NMR data.

$^1$H NMR (CDCl$_3$, 300 MHz) δ 7.85 (s, 2H, ph), 4.09 (m, 2H, —CHCH$_2$NPht), 3.93 (m, 1H, —CHCH$_2$NPht), 3.58 (s, 3H, —CO$_2$CH$_3$), 2.21 (s, 3H, —COCH$_3$)

$^{13}$C NMR (CDCl$_3$, 300 MHz) δ 200.5, 168.3, 166.2, 139.6, 139.2, 131.6, 131.3, 125.9, 125.7, 95.7, 62.3, 57.3, 36.7, 29.4, 19.8.

(11) Methyl 2-(1,3-dioxo-1,3-dihydro-benzo[f]isoindol-2-ylmethyl)-3-oxo-butyrate Methyl 2-(1,3-dioxo-1,3-dihydro-benzo[f]isoindol-2-ylmethyl)-3-oxo-butyrate was prepared (18 mg, 51%) in the same manner as described in the above example 6 (1) from methyl 3-(1,3-dioxo-1,3-dihydro-benzo[f]isoindol-2-yl)-2-(2-methyl-[1,3]dioxolan-2-yl)propionate (40 mg, 0.11 mmol) and pyridinium p-toluenesulfonate (5 mg), and the obtained product was identified with the following NMR data.

$^1$H NMR (CDCl$_3$, 300 MHz) δ 8.26 (s, 2H, ph), 7.98 (m, 2H, ph), 7.62 (m, 2H, ph), 4.18 (m, 2H, —CHCH$_2$NPht), 4.01 (dd, 1H, —CHCH$_2$NPht J=8.2 Hz, J'=6.6 Hz), 3.68 (s, 3H, —CO$_2$CH$_3$), 2.24 (s, 3H, —COCH$_3$)

$^{13}$C NMR (CDCl$_3$, 300 MHz) δ 200.8, 168.6, 167.9, 135.9, 130.7, 129.7, 127.8, 125.4, 124.9, 57.6, 53.3, 36.6, 29.4.

(12) Methyl 2-(1,3-dioxo-4-phenyl-1,3-dihydro-benzo[f]isoindol-2-ylmethyl)-3-oxo-butyrate Methyl 2-(1,3-dioxo-4-phenyl-1,3-dihydro-benzo[f]isoindol-2-ylmethyl)-3-oxo-butyrate was prepared (21 mg, 54%) in the same manner as described in the above example 6 (1) from methyl 3-(1,3-dioxo-4-phenyl-1,3-dihydro-benzo[f]isoindol-2-ylmethyl)-2-(2-methyl-[1,3]dioxolan-2-yl) propionate (44 mg, 0.12 mmol) and pyridinium p-toluenesulfonate (7 mg), and the obtained product was identified with the following NMR data.

$^1$H NMR (CDCl$_3$, 300 MHz) δ 8.30 (s, 1H, ph), 8.01 (d, 2H, ph, J=7.8 Hz), 7.73 (d, 2H, ph, J=8.3 Hz), 7.64 (t, 1H, ph, J=7.5 Hz), 7.49 (m, 4H, ph), 4.24 (m, 2H, —CHCH$_2$NPht), 4.08 (m, 1H, —CHCH$_2$NPht), 3.72 (s, 3H, —CO$_2$CH$_3$), 2.28 (s, 3H, —COCH$_3$)

$^{13}$C NMR (CDCl$_3$, 300 MHz) δ 200.8, 168.6, 157.6, 167.4, 140.9, 135.9, 135.8, 134.7, 130.7, 129.6, 129.0, 128.9, 128.5, 127.8, 125.8, 124.9, 123.9, 57.4, 53.2, 36.5, 29.2, 14.0.

(13) Methyl 2-(1,3-dioxo-1,3,4,5,6,7-hexahydro-isoindol-2-ylmethyl)-3-oxo-butyrate Methyl 2-(1,3-dioxo-1,3,4,5,6,7-hexahydro-isoindol-2-ylmethyl)-3-oxo-butyrate was prepared (360 mg, 31%) in the same manner as described in the above example 6 (1) from methyl 3-(1,3-dioxo-1,3,4,5,6,7-hexahydro-isoindol-2-ylmethyl)-2-(2-methyl-[1,3]dioxolan-2-yl)propionate (1.36 g, 4.21 mmol) and pyridinium p-toluenesulfonate (150 mg), and the obtained product was identified with the following NMR data.

$^1$H NMR (CDCl$_3$, 300 MHz) δ 3.89 (m, 3H, —CHCH$_2$NPht, —CHCH$_2$NPht), 3.67 (s, 3H, —CO$_2$CH$_3$), 2.24 (s, 4H, cyclohexene), 2.19 (s, 3H, —COCH$_3$), 1.69 (s, 4H, cyclohexene)

$^{13}$C NMR (CDCl$_3$, 300 MHz) δ 200.9, 170.8, 168.5, 142.1, 57.8, 53.1, 35.9, 29.1, 21.6, 20.2.

(14) Methyl 2-(2,5-dioxo-3-phenyl-2,5-dihydro-pyrrol-1-ylmethyl)-3-oxo-butyrate

Methyl 2-(2,5-dioxo-3-phenyl-2,5-dihydro-pyrrol-1-ylmethyl)-3-oxo-butyrate was prepared (114 mg, 14%) in the same manner as described in the above example 6 (1) from methyl 3-(2,5-dioxo-3-phenyl-2,5-dihydro-pyrrol-1-ylmethyl)-2-(2-methyl-[1,3]dioxolan-2-yl)propionate (1.00 g, 2.80 mmol) and pyridinium p-toluenesulfonate (100 mg), and the obtained product was identified with the following NMR data.

$^1$H NMR (CDCl$_3$, 300 MHz) δ 7.79 (m, 2H, ph), 7.44 (m, 3H, ph), 6.71 (s, 1H, —CH=C—), 4.07 (m, 2H, —CHCH$_2$NPht), 3.98 (m, 1H, —CHCH$_2$NPht), 3.24 (s, 3H, —CO$_2$CH$_3$), 2.26 (s, 3H, —COCH$_3$)

$^{13}$C NMR (CDCl$_3$, 300 MHz) δ 200.8, 170.5, 170.1, 168.5, 144.4, 131.7, 129.4, 129.0, 128.9, 124.3, 57.7, 53.3, 36.4, 29.4.

(15) Methyl 2-(2,5-dioxo-3,4-diphenyl-2,5-dihydro-pyrrol-1-ylmethyl)-3-oxo-butyrate Methyl 2-(2,5-dioxo-3,4-diphenyl-2,5-dihydro-pyrrol-1-ylmethyl)-3-oxo-butyrate was prepared (579 mg, 36%) in the same manner as described in the above example 6 (1) from methyl 3-(2,5-dioxo-3,4-diphenyl-2,5-dihydro-pyrrol-1-ylmethyl)-2-(2-methyl-[1,3]dioxolan-2-yl)propionate (1.40 g, 3.73 mmol) and pyridinium p-toluenesulfonate (100 mg), and the obtained product was identified with the following NMR data.

$^1$H NMR (CDCl$_3$, 300 MHz) δ 7.37 (dd, 4H, ph, J=7.6 Hz, J=1.2 Hz), 4.09 (m, 2H, —CHCH$_2$NPht), 3.96 (m, 1H, —CHCH$_2$NPht), 3.69 (s, 3H, —CO$_2$CH$_3$), 2.23 (s, 3H, —COCH$_3$)

$^{13}$C NMR (CDCl$_3$, 300 MHz) δ 200.9, 170.6, 168.6, 130.4, 128.9, 57.8, 53.3, 38.8, 29.3.

(16) Methyl 2-(5-fluoro-1,3-dioxo-1,3-dihydro-isoindol-2-ylmethyl)-3-oxo-butyrate Methyl 2-(5-fluoro-1,3-dioxo-1,3-dihydro-isoindol-2-ylmethyl)-3-oxo-butyrate was prepared (84 mg, 15%) in the same manner as described in the above example 6 (1) from methyl 3-(5-fluoro-1,3-dioxo-1,3-dihydro-isoindol-2-yl)-2-(2-methyl-[1,3]dioxolan-2-yl)propionate (0.63 g, 1.87 mmol) and pyridinium p-toluenesulfonate (51 mg), and the obtained product was identified with the following NMR data.

$^1$H NMR (CDCl$_3$, 300 MHz) δ 7.78 (dd, 1H, ph, J=9.0 Hz, J'=4.5 Hz), 7.44 (dd, 1H, ph, J=9.0 Hz, J'=2.2 Hz), 7.31 (m, 1H, ph), 4.11 (m, 2H, —CHCH$_2$NPht), 3.95 (dd, 1H, —CHCH$_2$NPht, J=8.2 Hz, J=6.5 Hz), 3.67 (s, 3H, —CO$_2$CH$_3$), 2.22 (s, 3H, —COCH$_3$)

$^{13}$C NMR (CDCl$_3$, 300 MHz) δ 200.6, 168.6, 168.4, 167.2, 165.1, 135.1, 127.9, 126.3, 126.2, 121.7, 111.9, 57.5, 53.3, 36.6, 29.3.

(17) Methyl 2-(5-chloro-1,3-dioxo-1,3-dihydro-isoindol-2-ylmethyl)-3-oxo-butyrate Methyl 2-(5-chloro-1,3-dioxo-1,3-dihydro-isoindol-2-ylmethyl)-3-oxo-butyrate was prepared (269 mg, 59%) in the same manner as described in the above example 6 (1) from methyl 3-(5-chloro-1,3-dioxo-1,3-dihydro-isoindol-2-yl)-2-(2-methyl-[1,3]dioxolan-2-yl)propionate (0.52 g, 1.48 mmol) and pyridinium p-toluenesulfonate (51 mg), and the obtained product was identified with the following NMR data.

$^1$H NMR (CDCl$_3$, 300 MHz) δ 7.71 (t, 1H, ph, J=1.4 Hz), 7.69 (s, 1H, ph), 7.61 (d, 1H, ph, J=7.9 Hz), 4.17–3.92 (m, 3H, —CHCH$_2$NPht, —CHCH$_2$NPht), 3.67 (s, 3H, —CO$_2$CH$_3$), 2.22 (s, 3H, —COCH$_3$)

$^{13}$C NMR (CDCl$_3$, 300 MHz) δ 250.6, 168.4, 167.2, 141.3, 134.8, 130.3, 125.1, 124.3, 57.4, 53.3, 36.5, 29.3.

(18) Methyl 2-(5-bromo-1,3-dioxo-1,3-dihydro-isoindol-2-ylmethyl)-3-oxo-butyrate Methyl 2-(5-bromo-1,3-dioxo-1,3-dihydro-isoindol-2-ylmethyl)-3-oxo-butyrate was prepared (106 mg, 24%) in the same manner as described in the above example 6 (1) from methyl 3-(5-bromo-1,3-dioxo-1,3-dihydro-isoindol-2-yl)-2-(2-methyl-[1,3]dioxolan-2-yl)propionate (0.46 g, 1.14 mmol) and pyridinium p-toluenesulfonate (50 mg), and the obtained product was identified with the following NMR data.

$^1$H NMR (CDCl$_3$, 300 MHz) δ 7.88 (d, 1H, ph, J=1.6 Hz), 7.78 (dd, 1H, ph, J=7.9 Hz, J'=1.6 Hz), 7.62 d, 1H, ph, J=7.9 Hz), 4.40–3.66 m, 3H, —CHCH$_2$NPht, —CHCH$_2$NPht, 3.86 s, 3H, —CO$_2$CH$_3$), 2.21 s, 3H, —COCH$_3$)

$^{13}$C NMR (CDCl$_3$, 300 MHz) δ 200.6, 168.3, 167.3, 166.8, 137.6, 133.8, 130.7, 129.5, 127.2, 125.2, 57.4, 53.3, 36.5, 29.3.

(19) Methyl 2-(1,3-dioxo-1,3-dihydro-benzo[e]isoindol-2-ylmethyl)-3-oxo-butyrate Methyl 2-(1,3-dioxo-1,3-dihydro-benzo[e]isoindol-2-ylmethyl)-3-oxo-butyrate was prepared (131 mg, 35%) in the same manner as described in the above example 6 (1) from methyl 3-(1,3-dioxo-1,3-dihydro-benzo[e]isoindol-2-ylmethyl)-2-(2-methyl-[1,3]dioxolan-2-yl)propionate (0.43 g, 1.17 mmol) and pyridinium p-toluenesulfonate (50 mg), and the obtained product was identified with the following NMR data.

$^1$H NMR (CDCl$_3$, 300 MHz) δ 8.75 (d, 1H, ph, J=6.2 Hz), 8.02 (d, 1H, ph, J=6.1 Hz), 7.82 (d, 1H, ph, J=7.7 Hz), 7.69 (d, 1H, ph, J=8.2 Hz), 7.57 (m, 2H, ph), 4.14 (m, 2H, —CHCH$_2$NPht), 4.00 (dd, 1H, —CHCH$_2$NPht, J=8.2 Hz, J'=6.4 Hz), 3.66 (s, 3H, —CO$_2$CH$_3$), 2.23 (s, 3H, —COCH$_3$)

$^{13}$C NMR (CDCl$_3$, 300 MHz) δ 200.9, 169.4, 168.7, 168.6, 136.9, 135.5, 131.4, 129.3, 129.1, 128.3, 127.3, 125.3, 118.8, 57.8, 53.3, 36.3, 29.4

(20) Ethyl 2-(1,3-dioxo-1,3,4,5,6,7-hexahydro-isoindol-2-ylmethyl)-3-oxo-butyrate Ethyl 3-(1,3-dioxo-1,3,4,5,6,7-hexahydro-isoindol-2-yl)-2-(2-methyl-[1,3]dioxolan-2-yl)propionate (866 mg, 2.57 mmol) was dissolved in a a solvent mixture of acetone/water (v/v=5/1), and a catalytic amount of p-toluenesulfonic acid monohydrate (190 mg, 0.76 mmol) was then added to the obtained solution. The resulting mixture was then refluxed at 80° C. for 4 days. After the reaction was completed, the reaction mixture where white solid were formed was washed with water. Acetone was removed by a vacuum evaporation, and the residue was extracted with dichloromethane. The combined organic layer was dried with anhydrous sulfate and then distilled under a reduced pressure in order to remove dichloromethane. The desired product was obtained (421 mg, 56%) by performing column chromatography (eluent: n-hexane/ethyl acetate=3/1). Rf=0.54 (eluent: n-hexane/ethyl acetate=1/1)

$^1$H NMR (CDCl$_3$, 300 MHz) δ 4.12 (q, 2H, —OCH$_2$CH$_3$, J=7.1 Hz), 3.88 (m, 2H, —CHCH$_2$NPht), 3.82 (m, 1H, —CHCH$_2$NPht), 2.24 (s, 4H, cyclohexane), 2.19 (s, 3H, —COCH$_3$), 1.70 (s, 4H, cyclohexane), 1.19 (t, 3H, —OCH$_2$CH$_3$, J=7.1 Hz)

$^{13}$C NMR (CDCl$_3$, 300 MHz) δ 201.1, 170.8, 168.0, 142.1, 62.2, 58.0, 35.8, 29.1, 21.6, 20.3, 14.3.

(21) Ethyl 2-(4-fluoro-1,3-dioxo-1,3-dihydro-isoindol-2-ylmethyl)-3-oxo-butyrate Ethyl 2-(4-fluoro-1,3-dioxo-1,3-dihydro-isoindol-2-ylmethyl)-3-oxo-butyrate was prepared (46 mg, 19%) in the same manner as described in the above example 6 (20) from ethyl 3-(4-fluoro-1,3-dioxo-1,3-dihydro-isoindol-2-yl)-2-(2-methyl-[1,3]dioxolan-2-yl)propionate (0.23 g, 0.67 mmol) and p-toluenesulfonic acid monohydrate (25 mg), and the obtained product was identified with the following NMR data.

$^1$H NMR (CDCl$_3$, 300 MHz) δ 7.64 (m, 2H, ph), 7.32 (t, 1H, ph, J=8.5 Hz), 4.10 (m, 4H, OCH$_2$CH$_3$, —CHCH$_2$NPht), 3.95 (t, 1H, —CHCH$_2$NPht, J=6.8 Hz), 2.23 (s, 3H, —COCH$_3$), 1.17 (t, 3H, —OCH$_2$CH$_3$, J=7.1 Hz)

$^{13}$C NMR (CDCl$_3$, 300 MHz) δ 200.9, 167.9, 167.1, 164.9, 59.7, 156.2, 137.3, 137.2, 134.4, 123.2, 122.9, 122.9, 120.1, 120.1, 62.6, 61.2, 57.6, 36.4, 29.3, 14.5, 14.3.

(22) Ethyl 2-(4,7-difluoro-1,3-dioxo-1,3-dihydro-isoindol-2-ylmethyl)-3-oxo-butyrate Ethyl 2-(4,7-difluoro-1,3-dioxo-1,3-dihydro-isoindol-2-ylmethyl)-3-oxo-butyrate was prepared (95 mg, 19%) in the same manner as described in the above example 6 (20) from ethyl 3-(4,7-difluoro-1,3-dioxo-1,3-dihydro-isoindol-2-yl)-2-(2-methyl-[1,3]dioxolan-2-yl)propionate (0.58 g, 1.57 mmol) and p-toluenesulfonic acid monohydrate (50 mg), and the obtained product was identified with the following NMR data.

$^1$H NMR (CDCl$_3$, 300 MHz) δ 7.32(m, 2H, ph), 4.09 (m, 4H, OCH$_2$CH$_3$, CHCH$_2$NPht), 3.92 (m, 1H, —CHCH$_2$NPht), 2.22 (s, 3H, —COCH$_3$), 1.19 (t, 3H, —OCH$_2$CH$_3$, J=7.1 Hz)

$^{13}$C NMR (CDCl$_3$, 300 MHz) δ 200.7, 167.8, 163.7, 152.3, 125.6, 125.5, 125.4, 125.4, 62.6, 57.3, 36.5, 29.2, 19.8, 14.4, 14.3.

(23) Ethyl 2-(4-nitro-1,3-dioxo-1,3-dihydro-isoindol-2-ylmethyl)-3-oxo-butyrate

Ethyl 2-(4-nitro-1,3-dioxo-1,3-dihydro-isoindol-2-ylmethyl)-3-oxo-butyrate was prepared (116 mg, 22%) in the same manner as described in the above example 6 (20) from ethyl 3-(4-nitro-1,3-dioxo-1,3-dihydro-isoindol-2-yl)-2-(2-methyl-[1,3]dioxolan-2-yl)propionate (0.38 g, 1.58 mmol) and p-toluenesulfonic acid monohydrate (25 mg), and the obtained product was identified with the following NMR data.

$^1$H NMR (CDCl$_3$, 300 MHz) δ 8.04 (m, 2H, ph), 7.84 (m, 1H, ph) 4.11 (m, 4H, OCH$_2$CH$_3$, CHCH$_2$NPht), 3.97 (t, 1H, —CHCH$_2$NPht J=6.5 Hz), 2.24 (s, 3H, —COCH$_3$), 1.18 (t, 3H, —OCH$_2$CH$_3$, J=7.1 Hz)

$^{13}$C NMR (CDCl$_3$, 300 MHz) 200.6, 167.8, 165.6, 162.9, 145.5, 135.9, 134.3, 129.1, 128.8, 127.6, 123.9, 62.6, 61.3, 57.7, 36.8, 29.4, 14.4.

(24) Ethyl 2-(5-nitro-1,3-dioxo-1,3-dihydro-isoindol-2-ylmethyl)-3-oxo-butyrate

Ethyl 2-(5-nitro-1,3-dioxo-1,3-dihydro-isoindol-2-ylmethyl)-3-oxo-butyrate was prepared (263 mg, 27%) in the same manner as described in the above example 6 (20) from ethyl 3-(5-nitro-1,3-dioxo-1,3-dihydro-isoindol-2-yl)-2-(2-methyl-[1,3]dioxolan-2-yl)propionate (1.11 g, 2.96 mmol) and p-toluenesulfonic acid monohydrate (100 mg), and the obtained product was identified with the following NMR data.

$^1$H NMR (CDCl$_3$, 300 MHz) δ 8.53 (d, 2H, ph, J=6.9 Hz), 7.98 (d, 1H, ph, J=7.5 Hz), 4.71–3.94 (m, 5H, —CHCH$_2$NPht, —OCH$_2$CH$_3$), 2.22 (s, 3H, —COCH$_3$), 1.17 (t, 3H, —OCH$_2$CH$_3$, J=5.4 Hz)

$^{13}$C NMR (CDCl$_3$, 300 MHz) 200.6, 177.8, 172.5, 167.7, 152.2, 133.8, 133.6, 129.8, 125.0, 119.1, 62.5, 57.2, 36.8, 29.3 19.7, 14.4, 14.3.

(25) Ethyl 2-(4-methyl-1,3-dioxo-1,3-dihydro-isoindol-2-ylmethyl)-3-oxo-butyrate Ethyl 2-(4-methyl-1,3-dioxo-1,3-dihydro-isoindol-2-ylmethyl)-3-oxo-butyrate was prepared (208 mg, 39%) in the same manner as described in the above example 6 (20) from ethyl 3-(4-methyl-1,3-dioxo-1,3-dihydro-isoindol-2-yl)-2-(2-methyl-[1,3]dioxolan-2-yl)propionate (0.52 g, 1.76 mmol) and p-toluenesulfonic acid monohydrate (50 mg), and the obtained product was identified with the following NMR data.

$^1$H NMR (CDCl$_3$, 300 MHz) δ 7.55 (d, 1H, ph, J=7.0 Hz), 7.48 (t, 1H, ph, J=7.3 Hz), 7.37 (d, 1H, ph, J=7.0 Hz), 4.36–3.94 (m, 5H, —CHCH$_2$NPht, —OCH$_2$CH$_3$, —CHCH$_2$NPht), 2.57 (s, 3H, CH$_3$), 2.21 (s, 3H, CH$_3$), 1.12 (t, 3H, —OCH$_2$CH$_3$, J=7.1 Hz)

$^{13}$C NMR (CDCl$_3$, 300 MHz) δ 201.1, 168.9, 168.3, 138.5, 136.9, 134.0, 132.6, 128.9, 121.4, 62.4, 57.8, 36.1, 29.2, 17.9, 14.3.

(26) Ethyl 2-(5-methyl-1,3-dioxo-1,3-dihydro-isoindol-2-ylmethyl)-3-oxo-butyrate Ethyl 2-(5-methyl-1,3-dioxo-1,3-dihydro-isoindol-2-ylmethyl)-3-oxo-butyrate was prepared (93 mg, 35%) in the same manner as described in the above example 6 (20) from ethyl 3-(5-methyl-1,3-dioxo-1,3-dihydro-isoindol-2-yl)-2-(2-methyl-[1,3]dioxolan-2-yl)propionate (0.38 g, 1.07 mmol) and p-toluenesulfonic acid monohydrate (30 mg), and the obtained product was identified with the following NMR data.

$^1$H NMR (CDCl$_3$, 300 MHz) δ 7.63 (d, 1H, ph, J=7.0 Hz), 7.55 (s, 1H, ph), 7.43 (d, 1H, ph, J=7.0 Hz), 4.19–3.93 (m, 5H, —CHCH$_2$NPht, —OCH$_2$CH$_3$, —CHCH$_2$NPht), 2.42 (s, 3H, CH$_3$), 2.01 (s, 3H, COCH$_3$), 1.14 (t, 3H, —OCH$_2$CH$_3$, J=7.1 Hz)

$^{13}$C NMR (CDCl$_3$, 300 MHz) δ 201.1, 171.3, 168.4, 145.9, 135.1, 129.5, 124.4, 123.8, 62.6, 61.4, 57.8, 36.3, 29.2, 22.3, 21.1, 14.5.

(27) Ethyl 2-(5-t-butyl-1,3-dioxo-1,3-dihydro-isoindol-2-ylmethyl)-3-oxo-butyrate Ethyl 2-(5-t-butyl-1,3-dioxo-1,3-dihydro-isoindol-2-ylmethyl)-3-oxo-butyrate was prepared (126 mg, 28%) in the same manner as described in the above example 6 (20) from ethyl 3-(5-t-butyl-1,3-dioxo-1,3-dihydro-isoindol-2-yl)-2-(2-methyl-[1,3]dioxolan-2-yl)propionate (0.52 g, 1.33 mmol) and p-toluenesulfonic acid monohydrate (50 mg), and the obtained product was identified with the following NMR data.

$^1$H NMR (CDCl$_3$, 300 MHz) δ 7.79 (s, 1H, ph), 7.66 (dd, 2H, ph, J=4.4 Hz), 4.09 (m, 4H, —CHCH$_2$NPht, —OCH$_2$CH$_3$), 3.95 (m, 1H, —CHCH$_2$NPht), 2.22 (s, 3H, —COCH$_3$), 1.29 (s, 9H, C(CH$_3$)$_3$), 1.16 (t, 3H, —OCH$_2$CH$_3$, J=7.1 Hz)

$^{13}$C NMR (CDCl$_3$, 300 MHz 201.1, 168.7, 168.3, 168.1, 159.2, 132.4, 131.5, 129.5, 123.6, 121.0, 62.4, 57.8, 36.1, 31.5, 14.3.

(28) Ethyl 2-(4-hydroxy-1,3-dioxo-1,3-dihydro-isoindol-2-ylmethyl)-3-oxo-butyrate Ethyl 2-(4-hydroxy-1,3-dioxo-1,3-dihydro-isoindol-2-ylmethyl)-3-oxo-butyrate was prepared (121 mg, 31%) in the same manner as described in the above example 6 (20) from ethyl 3-(4-hydroxy-1,3-dioxo-1,3-dihydro-isoindol-2-yl)-2-(2-methyl-[1,3]dioxolan-2-yl)propionate (0.46 g, 1.46 mmol) and p-toluenesulfonic acid monohydrate (50 mg), and the obtained product was identified with the following NMR data.

$^1$H NMR (CDCl$_3$, 300 MHz) δ 7.55 (s, 1H, OH), 7.51 (m, 1H, ph), 7.28 (d, 1H, ph, J=7.2 Hz), 7.08 (d, 1H, ph, J=8.3 Hz), 4.10–3.93 (m, 5H, OCH$_2$CH$_3$, CHCH$_2$NPht, —CHCH$_2$NPht), 2.22 (s, 3H, —COCH$_3$), 1.16 (t, 3H, —OCH$_2$CH$_3$, J=7.1 Hz)

$^{13}$C NMR (CDCl$_3$, 300 MHz) 200.8, 170.1, 167.9, 167.8, 155.1, 136.9, 132.2, 123.3, 116.5, 114.8, 62.9, 57.6, 36.1, 29.4, 14.3.

(29) Ethyl 2-(4,7-dichloro-1,3-dioxo-1,3-dihydro-isoindol-2-ylmethyl)-3-oxo-butyrate Ethyl 2-(4,7-dichloro-1,3-dioxo-1,3-dihydro-isoindol-2-ylmethyl)-3-oxo-butyrate was prepared (264 mg, 26%) in the same manner as described in the above example 6 (20) from ethyl 3-(4,7-dichloro-1,3-dioxo-1,3-dihydro-isoindol-2-yl)-2-(2-methyl-[1,3]dioxolan-2-yl)propionate (1.13 g, 2.80 mmol) and p-toluenesulfonic acid monohydrate (100 mg), and the obtained product was identified with the following NMR data.

$^1$H NMR (CDCl$_3$, 300 MHz) δ 7.84 (s, 2H, ph), 4.12 (m, 4H, —CHCH$_2$NPht, —OCH$_2$CH$_3$), 3.93 (m, 1H, —CHCH$_2$NPht), 2.21 (s, 3H, —COCH$_3$), 1.17 (t, 3H, —OCH$_2$CH$_3$, J=7.1 Hz)

$^{13}$C NMR (CDCl$_3$, 300 MHz) 200.6, 167.8, 166.2, 139.6, 161.2, 125.9, 125.6, 95.8, 62.5, 57.5, 36.6, 29.2, 19.8, 14.5, 14.3.

(30) Ethyl 2-(5,6-dichloro-1,3-dioxo-1,3-dihydro-isoindol-2-ylmethyl)-3-oxo-butyrate Ethyl 2-(5,6-dichloro-1,3-dioxo-1,3-dihydro-isoindol-2-ylmethyl)-3-oxo-butyrate was prepared (171 mg, 34%) in the same manner as described in the above example 6 (20) from ethyl 3-(5,6-dichloro-1,3-dioxo-1,3-dihydro-isoindol-2-yl)-2-(2-methyl-[1,3]dioxolan-2-yl)propionate (0.57 g, 1.42 mmol) and p-toluenesulfonic acid monohydrate (50 mg), and the obtained product was identified with the following NMR data.

$^1$H NMR (CDCl$_3$, 300 MHz) δ 7.83 (s, 2H, ph), 4.13–3.93 (m, 5H, —CHCH$_2$NPht, —OCH$_2$CH$_3$), 2.21 (s, 3H, COCH$_3$), 1.16 (t, 3H, OCH$_2$CH$_3$, J=7.1 Hz)

$^{13}$C NMR (CDCl$_3$, 300 MHz) δ 200.6, 177.8, 167.8, 139.6, 131.5, 125.9, 95.8, 62.5, 57.4, 36.7, 29.3, 19.8, 14.5.

(31) Ethyl 2-(1,3-dioxo-4-phenyl-1,3-dihydro-benzo[f]isoindol-2-ylmethyl)-3-oxo-butyrate Ethyl 2-(1,3-dioxo-4-phenyl-1,3-dihydro-benzo[f]isoindol-2-ylmethyl)-3-oxo-butyrate was prepared (214 mg, 22%) in the same manner as described in the above example 6 (20) from ethyl 3-(1,3-dioxo-4-phenyl-1,3-dihydro-benzo[f]isoindol-2-ylmethyl)-2-(2-methyl-[1,3]dioxolan-2-yl)propionate (1.09 g, 2.37 mmol) and p-toluenesulfonic acid monohydrate (100 mg), and the obtained product was identified with the following NMR data.

$^1$H NMR (CDCl$_3$, 300 MHz) δ 8.28 (s, 1H, ph), 7.98 (d, 1H, ph, J=7.9 Hz), 7.60 (d, 1H, ph, J=7.8 Hz), 7.55 (t, 1H, ph, J=7.0 Hz), 7.51 (m, 4H, ph), 7.29 (m, 2H, ph), 4.05 (m, 5H, —CHCH$_2$NPht, —OCH$_2$CH$_3$, —CHCH$_2$NPht), 2.16 (s, 3H, —COCH$_3$), 1.09 (t, 3H, —OCH$_2$CH$_3$, J=7.0 Hz)

$^{13}$C NMR (CDCl$_3$, 300 MHz) δ 201.1, 168.1, 167.6, 140.8, 135.8, 130.2, 129.5, 124.5, 62.3, 57.6, 36.5, 23.2, 14.3.

(32) Ethyl 2-(2,5-dioxo-3-phenyl-2,5-dihydro-pyrrol-1-ylmethyl)-3-oxo-butyrate

Ethyl 2-(2,5-dioxo-3-phenyl-2,5-dihydro-pyrrol-1-ylmethyl)-3-oxo-butyrate was prepared (77 mg, 23%) in the same manner as described in the above example 6 (20) from ethyl 3-(2,5-dioxo-3-phenyl-2,5-dihydro-pyrrol-1-ylmethyl)-2-(2-methyl-[1,3]dioxolan-2-yl)propionate (0.37 g, 1.05 mmol) and p-toluenesulfonic acid monohydrate (30 mg), and the obtained product was identified with the following NMR data.

$^1$H NMR (CDCl$_3$, 300 MHz) δ 7.83 (m, 2H, ph), 7.38 (m, 3H, ph), 6.55 (s, 1H, =CH), 4.13 (q, 2H, —OCH$_2$CH3), 3.98 (m, 2H, —CHCH$_2$NPht), 3.89 (m, 1H, —CHCH$_2$NPht), 2.20 (s, 3H, —COCH3),1.17 (t, 3H, —OCH$_2$CH3, J=7.1 Hz)

¹³C NMR (CDCl₃, 300 MHz) 200.9, 170.5, 170.1, 166.0, 144.3, 131.6, 129.4, 129.3, 129.0, 128.9, 124.2, 62.4, 57.7, 36.3, 29.3, 14.3.

(33) Ethyl 2-(2,5-dioxo-3,4-diphenyl-2,5-dihydro-pyrrol-1-ylmethyl)-3-oxo-butyrate Ethyl 2-(2,5-dioxo-3,4-diphenyl-2,5-dihydro-pyrrol-1-ylmethyl)-3-oxo-butyrate was prepared (204 mg, 23%) in the same manner as described in the above example 6 (20) from ethyl 3-(2,5-dioxo-3,4-diphenyl-2,5-dihydro-pyrrol-1-ylmethyl)-2-(2-methyl-[1,3]dioxolan-2-yl)propionate (1.00 g, 2.29 mmol) and p-toluenesulfonic acid monohydrate (100 mg), and the obtained product was identified with the following NMR data.

¹H NMR (CDCl₃, 300 MH) δ 7.37 (m, 4H, ph), 7.24 (m, 6H, ph), 4.10 (m, 4H, —CHCH₂NPht, —OCH₂CH₃), 3.94 (m, 1H, —CHCH₂NPht), 2.23 (s, 3H, —COCH₃), 1.19 (t, 3H, —OCH₂CH₃, J=7.1 Hz)

¹³C NMR (CDCl₃, 300 MHz) 201.0, 170.6, 168.1, 136.7, 130.4, 130.3, 128.9, 128.8, 62.4, 57.9, 36.7, 29.2, 14.4.

(34) Ethyl 2-(5-fluoro-1,3-dioxo-1,3-dihydro-isoindol-2-ylmethyl)-3-oxo-butyrate Ethyl 2-(5-fluoro-1,3-dioxo-1,3-dihydro-isoindol-2-ylmethyl)-3-oxo-butyrate was prepared (220 mg, 34%) in the same manner as described in the above example 6 (20) from ethyl 3-(5-fluoro-1,3-dioxo-1,3-dihydro-isoindol-2-yl)-2-(2-methyl-[1,3]dioxolan-2-yl)propionate (0.75 g, 2.13 mmol) and p-toluenesulfonic acid monohydrate (100 mg), and the obtained product was identified with the following NMR data.

¹H NMR (CDCl₃, 300M) δ 7.78 (dd, 1H, ph, J=9.0 Hz, J'=4.5 Hz), 7.44 (dd, 1H, ph, J=9.0 Hz, J'=2.2 Hz), 7.31 (m, 1H, ph), 4.10(m, 4H, —CHCH₂NPht, —OCH₂CH₃), 3.94 (m, 1H, —CHCH₂NPht), 2.22 (s, 3H, —COCH₃)

¹³C NMR (CDCl₃, 300 MHz) 164.9, 167.1, 166.8, 126.3, 126.1, 121.7, 121.4, 111.9, 111.5, 62.5, 57.6, 36.5, 29.2, 14.3.

(35) Ethyl 2-(5-chloro-1,3-dioxo-1,3-dihydro-isoindol-2-ylmethyl)-3-oxo-butyrate Ethyl 2-(5-chloro-1,3-dioxo-1,3-dihydro-isoindol-2-ylmethyl)-3-oxo-butyrate was prepared (171 mg, 34%) in the same manner as described in the above example 6 (20) from ethyl 3-(5-chloro-1,3-dioxo-1,3-dihydro-isoindol-2-yl)-2-(2-methyl-[1,3]dioxolan-2-yl)propionate (0.45 g, 1.22 mmol) and p-toluenesulfonic acid monohydrate (50 mg), and the obtained product was identified with the following NMR data.

¹H NMR (CDCl₃, 300 MH) δ 7.70 (m, 2H, ph, J=8.4 Hz), 7.61 (dd, 1H, ph, J=7.9 Hz, J=1.7 Hz), 4.09 (m, 4H, —CHCH₂NPht, —OCH₂CH₃), 3.94 (dd, 1H, —CHCH2NPht J=8.3 Hz, J=6.5 Hz), 2.21 (s, 3H, —COCH₃), 1.16 (t, 3H, —OCH₂CH₃, J=7.1 Hz)

¹³C NMR (CDCl₃, 300 MHz) 200.8, 167.9, 167.2, 141.2, 134.6, 133.8, 130.3, 125.0, 124.2, 62.4, 57.5, 36.5, 29.3, 14.3.

(36) Ethyl 2-(5-bromo-1,3-dioxo-1,3-dihydro-isoindol-2-ylmethyl)-3-oxo-butyrate

Ethyl 2-(5-bromo-1,3-dioxo-1,3-dihydro-isoindol-2-ylmethyl)-3-oxo-butyrate was prepared (168 mg, 31%) in the same manner as described in the above example 6 (20) from ethyl 3-(5-bromo-1,3-dioxo-1,3-dihydro-isoindol-2-yl)-2-(2-methyl-[1,3]dioxolan-2-yl)propionate (0.41 g, 1.36 mmol) and p-toluenesulfonic acid monohydrate (50 mg), and the obtained product was identified with the following NMR data.

¹H NMR (CDCl₃, 300 MHz) δ 7.87 (d, 1H, ph, J=1.6 Hz), 7.80 (dd, 1H, ph, J=7.9 Hz, J=1.6 Hz), 7.63 (d, 1H, ph, J=6.5 Hz), 4.11 (m, 4H, —CHCH₂NPht, —OCH₂CH₃), 3.93 (m, 1H, —CHCH₂NPht), 2.21 (s, 3H, —COCH₃), 1.16 (t, 3H, —OCH₂CH₃, J=7.1 Hz)

¹³C NMR (CDCl₃, 300 MHz) 200.8, 167.9, 166.8, 137.6, 130.7, 127.1, 125.2, 62.5, 57.5, 36.5, 29.3, 14.3.

(37) Ethyl 2-(1,3-dioxo-1,3-dihydro-benzo[e]isoindol-2-ylmethyl)-3-oxo-butyrate

Ethyl 2-(5-bromo-1,3-dioxo-1,3-dihydro-isoindol-2-ylmethyl)-3-oxo-butyrate was prepared (223 mg, 52%) in the same manner as described in the above example 6 (20) from ethyl 3-(1,3-dioxo-1,3-dihydro-benzo[e]isoindol-2-ylmethyl)-2-(2-methyl-[1,3]dioxolan-2-yl)propionate (0.49 g, 1.27 mmol) and p-toluenesulfonic acid monohydrate (50 mg), and the obtained product was identified with the following NMR data.

¹H NMR (CDCl₃, 300 MHz) δ 8.77 (d, 1H, ph, J=8.4 Hz), 8.05 (d, 1H, ph, J=8.3 Hz), 7.84 (d, 1H, ph, J=7.7 Hz), 7.72 (d, 1H, ph, J=8.2 Hz), 7.57 (m, 2H, ph), 4.10 (m, 5H, —CHCH₂NPht, —CHCH₂NPht, —OCH₂CH₃), 2.23 (s, 3H, —COCH₃), 1.14 (t, 3H, —OCH₂CH₃, J=7.1 Hz)

¹³C NMR (CDCl₃, 300 MHz) 201.1, 169.4, 168.8, 168.1, 136.9, 135.9, 131.5, 129.9, 129.2, 128.3, 127.5, 118.8, 62.4, 57.9, 57.2, 36.2, 29.4, 14.3

(38) Ethyl 2-(4-methoxy-1,3-dioxo-1,3-dihydro-isoindol-2-ylmethyl)-3-oxo-butyrate Ethyl 3-(4-hydroxy-1,3-dioxo-1,3-dihydro-isoindol-2-yl)-2-(2-methyl-[1,3]-ioxolan-2-yl)propionate (40 mg, 0.11 mmol) was dissolved in 1 mL of 1,4-dioxane, and dimethylsulfate (22 mg, 0.13 mmol) and K₂CO₃ (35 mg, 0.25 mmol) were then added to the obtained solution. The resulting mixture was then refluxed at 70° C. for 30 minutes. After the reaction was completed, 1 mL of water was added to the reaction mixture and the mixture was then extracted with ethyl acetate (2 mL×3). The combined organic layer was dried with anhydrous sulfate and distilled under a reduced pressure. The desired product was obtained (24 mg, 61%) by performing column chromatography (eluent: n-hexane/ethyl acetate=3/1).

¹H NMR (CDCl₃, 300 MHz) δ 7.59 (t, 1H, ph, J=7.3 Hz), 7.35 (d, 2H, ph, J=7.3 Hz), 7.11 (d, 1H, ph, J=8.4 Hz), 4.15–4.05 (m, 5H, —CHCH₂NPht, —OCH₂CH₃, —CHCH₂NPht), 3.94 (s, 3H, OCH₃), 2.21 (s, 3H, —COCH₃), 1.14 (t, 3H, —OCH₂CH₃, J=7.1 Hz)

¹³C NMR (CDCl₃, 300 MHz) 201.1, 168.1, 167.8, 166.9, 157.2, 136.7, 134.5, 118.1, 117.6, 116.0, 62.6, 57.8, 56.7, 36.2, 29.1, 14.2

(39) Ethyl 2-(4-acetoxy-1,3-dioxo-1,3-dihydro-isoindol-2-ylmethyl)-3-oxo-butyrate Ethyl 3-(4-hydroxy-1,3-dioxo-1,3-dihydro-isoindol-2-yl)-2-(2-methyl-[1,3]dioxolan-2-yl)propionate (102.4 mg, 0.34 mmol) was dissolved in dichloromethane, and pyridine (55 μl, 0.682 mmol) and acetyl chloride (49 μl, 0.68 mmol) were then slowly added dropwise to the obtained solution at 0° C. The resulting mixture was then stirred at the same temperature for 10 minutes. After the reaction was completed, the reaction mixture was washed with water and then the aqueous layer was extracted with dichloromethane. The combined organic layer was dried with anhydrous sulfate and distilled under a reduced pressure. The desired product (64 mg, 54%) was obtained by performing column chromatography (eluent: n-hexane/ethyl acetate=3/1).

¹H NMR (CDCl₃, 300 MHz) δ 7.65 (m, 2H, ph), 7.29 (m, 1H, ph), 4.14–4.02 (m, 4H, —CHCH₂NPht, —OCH₂CH₃), 3.94 (m, 1H, —CHCH₂NPht), 2.33 (s, 3H, —COCH₃), 1.15 (t, 3H, —OCH₂CH₃, J=7.1 Hz)

¹³C NMR (CDCl₃, 300 MHz) 200.8, 168.8, 167.9, 165.8, 147.1, 136.3, 133.8, 123.1, 121.5, 62.4, 57.6, 36.4, 19.4, 21.0, 14.2.

(40) Allyl 2-(4-fluoro-1,3-dioxo-1,3-dihydro-isoindol-2-ylmethyl)-3-oxo-butyrate Allyl 3-(4-fluoro-1,3-dioxo-1,3-dihydro-isoindol-2-yl)-2-(2-methyl-[1,3]dioxolan-2-yl)propionate (331 mg, 0.91 mmol) was dissolved in a a solvent mixture of acetone/water (v/v=5/1), and catalyst amount of p-toluenesulfonic acid anhydride was added to the obtained solution. The resulting mixture was refluxed at 80° C. for 18 hours. After the reaction was completed, the reaction mixture was washed with water, and then acetone was removed by distilling under a reduced pressure. The residue was extracted with dichloromethane. The combined organic layer was dried with anhydrous sulfate and distilled under a reduced pressure. The desired product was obtained (131.2 mg, 31%) by performing column chromatography (eluent: n-hexane/ethyl acetate=2/1).

¹H NMR (CDCl₃, 300 MHz) δ 7.66 (m, 1H, ph), 7.58 (d, 1H, ph, J=7.2 Hz), 7.31 (t, 1H, ph, J=8.4 Hz), 5.76 (m, 1H, CH₂CH=CH₂), 5.15 (m, 2H, CH₂CH=CH₂), 4.54 (d, 1H, CH₂CH=CH₂, J=5.9 Hz), 4.11–3.97 (m, 3H, —CHCH₂NPht, —CHCH₂NPht), 2.22 (s, 3H, —COCH₃)

¹³C NMR (CDCl₃, 300 MHz) δ 200.6, 167.6, 166.9, 164.8, 159.7, 137.3, 134.4, 131.4, 123.1, 120.1, 119.9, 117.9, 66.9, 57.4, 36.4, 29.3.

(41) Allyl 2-(4,7-difluoro-1,3-dioxo-1,3-dihydro-isoindol-2-ylmethyl)-3-oxo-butyrate Allyl 2-(4,7-difluoro-1,3-dioxo-1,3-dihydro-isoindol-2-ylmethyl)-3-oxo-butyrate was prepared (86 mg, 23%) in the same manner as described in the above Example 6 (40) from allyl 3-(4,7-difluoro-1,3-dioxo-1,3-dihydro-isoindol-2-yl)-2-(2-methyl-[1,3]dioxolan-2-yl)propionate (0.35 g, 0.92 mmol) and p-toluenesulfonic acid monohydrate (40 mg), and the obtained product was identified with the following NMR data.

¹H NMR (CDCl₃, 300 MHz) δ 7.33 (t, 2H, ph, J=5.5 Hz), 5.55 (m, 1H, CH₂CH=CH₂), 5.26 (m, 2H, CH₂CH=CH₂), 4.55 (d, 1H, CH₂CH=CH₂, J=6.0 Hz), 4.11–3.93 (m, 3H, —CHCH₂NPht, —CHCH₂NPht), 2.23 (s, 3H, —COCH₃)

¹³C NMR (CDCl₃, 300 MHz) δ 200.5, 167.5, 163.8, 154.0, 131.4, 125.4, 120.0, 118.9, 67.0, 57.2, 36.5, 29.3

2. Separation and Purification of Reductase

Example 7

Separation and Purification of Reductase From *Kluyveromyces marxianus*

*Kluyveromyces marxianus* was cultivated in 8 L of YM culture medium at 30° C. for 3 days until O.D$_{600}$ became about 7.0. The cultivated cells were collected by centrifuging at 3,000 g for 10 minutes. The obtained cells were dissolved in 500 mL of diluted solution (20 mM Tris-HCl, pH 8.0), and the remained culture medium was centrifuged to remove. After 1 mM of phenylmethylsulfonyl fluoride (PMSF, Sigma) was added into the diluted solution, a French Pressure Cell Press was operated at a pressure of 11.0 kbar and followed by operating a Branson sonifier (Model 450) 5 times for 5 minutes, in order to crush the cells.

The obtained cell extract was centrifuged at 25,000 g for 30 minutes, the components of the supernatant was then separated by an anion exchange chromatography (Q-Sepharose (용어가적합한지검토하여주시기바랍니다) FPLC, LKB Pharmacia), and then activities of the substrate of each eluent was determined with HPLC (Waters) (See FIG. 3). Solutions which exhibited an activity were combined, ammonium sulfate (AMS) was then added to the solution so as the concentration of AMS to be 1.0M, and then separated with phenyl Sepharose. The eluent in which activity exhibited was separated by performing high trap blue Sepharose which is an affinity column, and was finally separated using gel filtering chromatography (Superdex-75, FPLC, LKB Pharmacia).

When electrophoresis of the purified protein was performed in 12% SDS-polyacryl amide gel, a protein band corresponding to a molecular weight of about 40 kDa was identified (see FIG. 2). The amount of protein in each column step was measured by Bradford Analysis (see FIG. 3). Sequence of the amino acid terminus was identified by which the protein was transferred to a PVDF membrane.

Sequence of the amino acid terminus: ¹Thr-Phe-Thr-Val-Val-Thr-⁷Gly

3. Reduction by Reductase

Example 8

Reduction by Reductase of *Kluyveromyces marxianus*

A solution in which 1.14 mg (2.0 eq) of β-NADPH was dissolved in 10 μl of Na-phosphate buffer solution was suspended in 190 μl of Na-phosphate buffer solution (100 mM, pH 6.8, Sigma). After adding 50 μl of reductase solution and a substrate compound (12.5 μl 10 mg in 0.5 ml of ethanol), the resulting mixture was reacted in a stirring cultivator at 30° C. After the reaction was completed, 100 μl of the reaction mixture was taken and extracted with the same amount of ethyl acetate. 50 μl of organic layer was taken from the organic extract, diluted with 1 ml of movile phase (hexane:isopropylalcohol=90:10) and then analyzed by HPLC.

Representative products obtained through the above procedure and structures thereof were identified from the following ¹H NMR data.

(1) (2S,3R) ethyl 2-(1,3-dioxo-1,3-dihydro-isoindol-2-ylmethyl)-3-hydroxy-butyrate ¹H NMR (CDCl₃, 300 MHz) δ 7.73 (m, 4H, ph), 4.00 (m, 5H, CHCH₂Npht, —CHOH, —OCH₂CH₃), 2.62 (m, 1H, —CHCH₂), 1.19 (d, 3H, J=6.1 Hz —CH₃CH), 1.12 (t, 3H, J=7.1 Hz, —OCH₂CH₃)

(2) (2R,3R) ethyl 2-(1,3-dioxo-1,3-dihydro-isoindol-2-ylmethyl)-3-hydroxy-butyrate ¹H NMR (CDCl₃, 300 MHz) δ 7.73 (m, 4H, ph), 3.98 (m, 5H, CHCH₂Npht, —CHOH, —OCH₂CH₃), 2.76 (m, 1H, —CHCH₂), 1.26 (d, 3H, J=6.5 Hz —CH₃CH), 1.10 (t, 3H, J=7.1 Hz, —OCH₂CH₃)

(3) (2S,3R) ethyl 2-(3,6-difluoro-1,3-dioxo-1,3-dihydro-isoindol-2-ylmethyl)-3-hydroxy-butyrate ¹H NMR (CDCl₃, 300 MHz) δ 7.41 (t, 2H, ph, J=5.5 Hz), 4.07 (m, 5H, CHCH₂Npht, —CHOH, —OCH₂CH₃), 2.69 (m, 1H, —CHCH₂), 1.17 (m, 6H, —CH₃CH, —OCH₂CH₃)

(4) (2S,3R) ethyl 2-(3-fluoro-1,3-dioxo-1,3-dihydro-isoindol-2-ylmethyl)-3-hydroxy-butyrate $^1$H NMR (CDCl$_3$, 300 MHz) δ 7.50 (t, 3H, ph), 4.01 (m, 5H, CHCH$_2$Npht, —CHOH, —OCH$_2$CH$_3$), 2.38 (m, 1H, —CHCH$_2$), 1.19 (t, 3H, J=6.3 Hz, —OCH$_2$CH$_3$), 1.13 (d, 3H, J=7.2 Hz, —OCH$_2$CH$_3$)

(5) (2R,3R) ethyl 2-(3-fluoro-1,3-dioxo-1,3-dihydro-isoindol-2-ylmethyl)-3-hydroxy-butyrate $^1$H NMR (CDCl$_3$, 300 MHz) δ 7.49 (t, 3H, ph), 3.99 (m, 5H, CHCH$_2$Npht, —CHOH, —OCH$_2$CH$_3$), 2.76 (m, 1H, —CHCH$_2$), 1.26 (t, 3H, J=6.5 Hz, —OCH$_2$CH$_3$), 1.10 (d, 3H, J=7.1 Hz, —OCH$_2$CH$_3$)

(6) (2S,3R) methyl 2-(3-fluoro-1,3-dioxo-1,3-dihydro-isoindol-2-ylmethyl)-3-hydroxy-butyrate $^1$H NMR (CDCl$_3$, 300 MHz) δ 7.50 (t, 3H, ph), 4.00 (m, 5H, CHCH$_2$Npht, —CHOH), 3.63 (m, 3H, —OCH$_3$), 2.63 (m, 1H, —CHCH$_2$), 1.19 (t, 3H, J=6.2 Hz, —OCH$_2$CH$_3$)

(7) (2R,3R) methyl 2-(3-fluoro-1,3-dioxo-1,3-dihydro-isoindol-2-ylmethyl)-3-hydroxy-butyrate $^1$H NMR (CDCl$_3$, 300 MHz) δ 7.45 (t, 3H, ph), 4.08 (m, 5H, CHCH$_2$Npht, —CHOH), 3.63 (m, 3H, —OCH$_3$), 2.77 (m, 1H, —CHCH$_2$), 1.26 (t, 3H, J=6.2 Hz, —OCH$_2$CH$_3$)

(8) (2S,3R) ethyl 2-(3-methoxy-1,3-dioxo-1,3-dihydro-isoindol-2-ylmethyl)-3-hydroxy-butyrate $^1$H NMR (CDCl$_3$, 300 MHz) δ 7.61 (dd, 1H, J=7.3 Hz, J=8.4 Hz, ph), 7.38 (d, 1H, J=7.3 Hz, ph), 7.16 (d, 1H, J=8.4 Hz, ph), 3.98 (m, 5H, CHCH$_2$Npht, —CHOH, —OCH$_2$CH$_3$), 3.92 (s, 3H, —PhOCH$_3$), 2.73 (m, 1H, —CHCH$_2$), 1.24 (t, 3H, J=6.4 Hz, —OCH$_2$CH$_3$). 1.10 (d, 3H, J=7.1 Hz, —OCH$_2$CH$_3$)

(9) (2R,3R) ethyl 2-(3-methoxy-1,3-dioxo-1,3-dihydro-isoindol-2-ylmethyl)-3-hydroxy-butyrate $^1$H NMR (CDCl$_3$, 300 MHz) δ 7.61 (dd, 1H, J=7.3 Hz, J=8.4 Hz, ph), 7.37 (d, 1H, J=7.3 Hz, ph), 7.15 (d, 1H, J=8.4 Hz, ph), 3.98 (m, 5H, CHCH$_2$Npht, —CHOH, —OCH$_2$CH$_3$), 3.96 (s, 3H, —PhOCH$_3$), 2.59 (m, 1H, —CHCH$_2$), 1.18 (t, 3H, J=6.4 Hz, —OCH$_2$CH$_3$). 1.14 (d, 3H, J=7.1 Hz, —OCH$_2$CH$_3$)

Reduction by reductase in accordance with the present invention is a useful method for preparing optically pure compounds. Particularly, while a reaction using Baker's Yeast(BY) which is generally used in reduction of carbonyl group of β-keto ester generates (S)-3-hydroxy compound, the reduction using the reductase of *Kluyveromyces marxianus* according to the present invention mainly generates (R)-3-hydroxy compounds.

In the present invention, α-substituted β-hydroxy ester having (2S,3R) or (2R,3R) stereochemistry was provided through a reduction reaction using properties of microorganism. Such compounds can be used as an intermediate for synthesizing carbapenem group antibiotics.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A compound represented by the following formula (Ia) or (Ib):

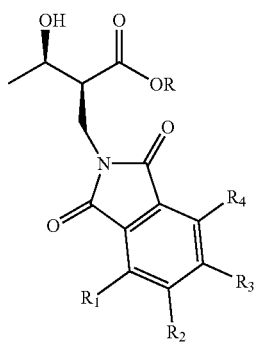

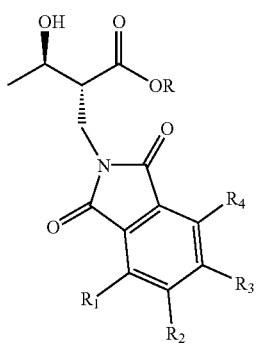

wherein, R represents a saturated or unsaturated alkyl group selected from the group consisting of methyl, ethyl, propyl, isopropyl, isobutyl and allyl, or an aryl group; and R$_1$, R$_2$, R$_3$ and R$_4$ are independently selected from the group consisting of hydrogen atom, a halogen atom, an alkyl group having 1–4 carbon atoms, hydroxy, an alkoxy group having 1–4 carbon atoms, an ester group, phenyl and combinations thereof wherein at least one of R$_1$, R$_2$, R$_3$ and R$_4$ is not hydrogen or methyl.

2. The compound according to claim 1, wherein the R is methyl group.

3. The compound according to claim 2, which is (2S,3R) methyl 2-(4-fluoro-1,3-dioxo-1,3-dihydro-isoindol-2-ylmethyl)-3-hydroxy-butyrate, (2S,3R) methyl 2-(4,7-difluoro-1,3-dioxo-1,3-dihydro-isoindol-2-ylmethyl)-3-hydroxy-butyrate, (2S,3R) methyl 2-(4-methyl-1,3-dioxo-1,3-dihydro-isoindol-2-ylmethyl)-3-hydroxy-butyrate, (2S,3R) methyl 2-(5-methyl-1,3-dioxo-1,3-dihydro-isoindol-2-ylmethyl)-3-hydroxy-butyrate, (2S,3R) methyl 2-(1,3-dioxo-1,3,4,5,6,7-hexahydro-isoindol-2-ylmethyl)-3-hydroxy-butyrate, (2S,3R) methyl 2-(5-fluoro-1,3-dioxo-1,3-dihydro-isoindol-2-ylmethyl)-3-hydroxy-butyrate, (2S,3R) methyl 2-(4-methoxy-1,3-dioxo-1,3-dihydro-isoindol-2-ylmethyl)-3-hydroxy-butyrate, (2R,3R) methyl 2-(1,3-dioxo-1,3-dihydro-isoindol-2-ylmethyl)-3-hydroxy-butyrate, (2R,3R) methyl 2-(4-fluoro-1,3-dioxo-1,3-dihydro-isoindol-2-ylmethyl)-3-hydroxy-butyrate, (2R,3R) methyl 2-(4,7-difluoro-1,3-dioxo-1,3-dihydro-isoindol-2-ylmethyl)-3-hydroxy-butyrate, (2R,3R) methyl 2-(4-methyl-1,3-dioxo-1,3-dihydro-isoindol-2-ylmethyl)-3-hydroxy-butyrate, (2R,3R) methyl 2-(5-methyl-1,3-dioxo-1,3-dihydro-isoindol-2-ylmethyl)-3-hydroxy-butyrate, (2R,3R) methyl 2-(1,3-dioxo-1,3,4,5,6,7- hexahydro-isoindol-2-ylmethyl)-3-hydroxy-butyrate, (2R, 3R) methyl 2-(5-fluoro-1,3-dioxo-1,3-dihydro-isoindol-2-ylmethyl)-3-hydroxy-butyrate or (2R,3R) methyl 2-(4-methoxy-1,3-dioxo-1,3-dihydro-isoindol-2-ylinethyl)-3-hydroxy-butyrate.

4. The compound according to claim 1, wherein the R is ethyl group.

5. The compound according to claim 4, which is (2S,3R) ethyl 2-(4-fluoro-1,3-dioxo-1,3-dihydro-isoindol-2-ylmethyl)-3-hydroxy-butyrate, (2S,3R) ethyl 2-(4,7-difluoro-1,3-dioxo-1,3-dihydro-isoindol-2-ylmethyl)-3-hydroxy-butyrate, (2S,3R) ethyl 2-(4-methyl-1,3-dioxo-1,3-dihydro-isoindol-2-ylmethyl)-3-hydroxy-butyrate, (2S,3R) ethyl 2-(5-methyl-1,3-dioxo-1,3-dihydro-isoindol-2-ylmethyl)-3-hydroxy-butyrate, (2S,3R) ethyl 2-(5-fluoro-1,3-dihydro-isoindol-2-ylmethyl)-3-hydroxy-butyrate, (2S,3R) ethyl 2-(4-methoxy-1,3-dioxo-1,3-dihydro-isoindol-2-ylmethyl)-3-hydroxy-butyrate, (2R,3R) ethyl 2-(1,3-dioxo-1,3-dihydro-isoindol-2-ylmethyl)-3-hydroxy-butyrate, (2R,3R) ethyl 2-(4-fluoro-1,3-dioxo-1,3-dihydro-isoindol-2-ylmethyl)-3-hydroxy-butyrate, (2R,3R) ethyl 2-(4,7-difluoro-1,3-dioxo-1,3-dihydro-isoindol-2-ylmethyl)-3-hydroxy-butyrate, (2R,3R) ethyl 2-(4-methyl-1,3-dioxo-1,3-dihydro-isoindol-2-ylmethyl)-3-hydroxy-butyrate, (2R,3R) ethyl 2-(5-methyl-1,3-dioxo-1,3-dihydro-isoindol-2-ylmethyl)-3-hydroxy-butyrate, (2R,3R) ethyl 2-(5-fluoro-1,3-dioxo-1,3-dihydro-isoindol-2-ylmethyl)-3-hydroxy-butyrate or (2R,3R) ethyl 2-(4-methoxy-1,3-dioxo-1,3-dihydro-isoindol-2-ylmethyl)-3-hydroxy-butyrate.

6. A preparation method of the compound represented by the formula (Ia) or (Ib) by reducing the compound represented by the formula (VI) with a reductase of *Kluyveromyces marxianus*

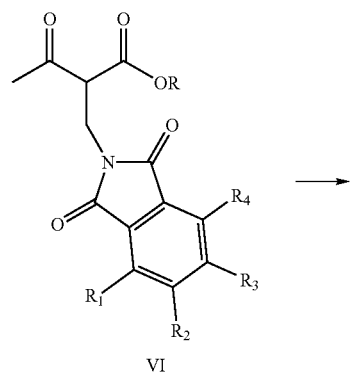

VI

-continued

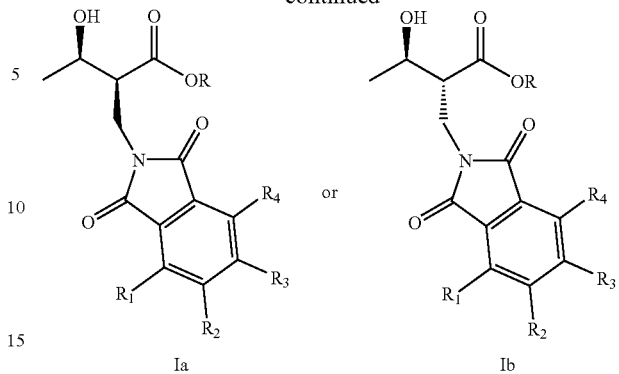

Ia or Ib wherein, R represents a saturated or unsaturated alkyl group selected from the group consisting of methyl, ethyl, propyl, isopropyl, isobutyl and allyl, or an aryl group; and $R_1$, $R_2$, $R_3$ and $R_4$ are independently selected from the group consisting of hydrogen atom, a halogen atom, an alkyl group having 1–4 carbon atoms, hydroxy, an alkoxy group having 1–4 carbon atoms, an ester group, phenyl and combinations thereof.

7. The preparation method according to claim 6, comprising the steps of mixing the compound of the formula (VI) with β-NADPH and a buffer solution of pH 5.0–8.0, followed by adding the reductase to the resulting mixture, and then carrying out the reduction reaction at 20–40° for 5 hours to 5 days.

8. The compound of claim 1, wherein R is phenyl.

9. The compound of claim 1, wherein one or more of $R_1$, $R_2$, $R_3$ and $R_4$ is independently selected from methyl and ethyl.

10. The compound of claim 1, wherein one or more of $R_1$, $R_2$, $R_3$ and $R_4$ is an acetoxy group.

11. The preparation method of claim 6, wherein R is phenyl.

12. The preparation method of claim 6, wherein one or more of $R_1$, $R_2$, $R_3$ and $R_4$ is independently selected from methyl and ethyl.

13. The preparation method of claim 6, wherein one or more of $R_1$, $R_2$, $R_3$ and $R_4$ is an acetoxy group.

* * * * *